US010501497B2

(12) United States Patent
Bridon et al.

(10) Patent No.: US 10,501,497 B2
(45) Date of Patent: Dec. 10, 2019

(54) CYCLIC POLYPEPTIDES, METHOD FOR OBTAINING THEM AND THE THERAPEUTIC USE THEREOF

(71) Applicant: AXOLTIS PHARMA, Clermont-Ferrand (FR)

(72) Inventors: Dominique Bridon, San Francisco, CA (US); Stéphane Gobron, Dallet (FR)

(73) Assignee: AXOLTIS PHARMA, Clermont-Ferrand (FR)

( * ) Notice: Subject to any disclaimer, the term of this patent is extended or adjusted under 35 U.S.C. 154(b) by 0 days.

(21) Appl. No.: 15/762,921

(22) PCT Filed: Sep. 23, 2016

(86) PCT No.: PCT/FR2016/052422
§ 371 (c)(1),
(2) Date: Mar. 23, 2018

(87) PCT Pub. No.: WO2017/051135
PCT Pub. Date: Mar. 30, 2017

(65) Prior Publication Data
US 2018/0265549 A1 Sep. 20, 2018

(30) Foreign Application Priority Data
Sep. 25, 2015 (FR) ...................................... 15 59084

(51) Int. Cl.
*C07K 7/64* (2006.01)
*A61K 38/00* (2006.01)
*C07K 14/78* (2006.01)

(52) U.S. Cl.
CPC ................ *C07K 7/64* (2013.01); *A61K 38/00* (2013.01); *C07K 14/78* (2013.01)

(58) Field of Classification Search
None
See application file for complete search history.

(56) References Cited

U.S. PATENT DOCUMENTS

| 6,995,140 | B1 | 2/2006 | Meiniel et al. |
| 2011/0178023 | A1 | 7/2011 | Meiniel et al. |
| 2017/0246247 | A1 | 8/2017 | Meiniel et al. |

FOREIGN PATENT DOCUMENTS

| EP | 0478101 | 4/1992 |
| WO | WO-2008/090285 | 7/2008 |

OTHER PUBLICATIONS

Sakka, Laurent, et al. "SCO-Spondin Derived Peptide NX210 Induces Neuroprotection In Vitro and Promotes Fiber Regrowth and Functional Recovery after Spinal Cord Injury." PLoS ONE, vol. 9, No. 3, Mar. 25, 2014, pp. 1-8., doi:10.1371/journal.pone.0093179.
F., El-Bitar, et al. "Effects of SCO-Spondin Thrombospondin Type 1 Repeats (TSR) in Comparison to Reissner's Fiber Material on the Differentiation of the B104 Neuroblastoma Cell Line." Cell and Tissue Research, vol. 304, No. 3, 2001, pp. 361-369., doi:10.1007/s004410100383.
Gobron, Stéphane, et al. "Subcommissural Organ/Reissner's Fiber Complex: Characterization of SCO-Spondin, a Glycoprotein with Potent Activity on Neurite Outgrowth." Glia, vol. 32, No. 2, 2000, pp. 177-191., doi:10.1002/1098-1136(Nov. 2000)32:23.0.co;2-v.
Meiniel, Annie. "SCO-Spondin, a Glycoprotein of the Subcommissural Organ/Reissner's Fiber Complex: Evidence of a Potent Activity on Neuronal Development in Primary Cell Cultures." Microscopy Research and Technique, vol. 52, No. 5, 2001, pp. 484-495., doi:10.1002/1097-0029(Mar. 1, 2001)52:53.0.co;2-0.
International Search Report in International Application No. PCT/FR2016/052422 dated Feb. 3, 2017.
Maulik Trivedi, et al.: "The Role of Thiols and Disulfides on Protein Stability", Curr. Protein Pept. Sci, vol. 10, No. 6, Dec. 1, 2009 (Dec. 1, 2009), pp. 614-625, XP055234745, NL ISSN: 389-2037, DOI: 10/2174/138920309789630534 p. 5, paragraph.

*Primary Examiner* — John D Ulm
(74) *Attorney, Agent, or Firm* — B. Aaron Schulman, Esq.; Stites & Harbison, PLLC

(57) ABSTRACT

The invention relates to a polypeptide #including the following amino acid sequence: W-S-X1-W-X2-X3-C-S-X4-C-G (SEQ ID NO: 59), wherein X1, X2 and X3 are, independently of one another, S or G, X4 is R-S or V-S or V-T or R-T, and both cysteines form a disulfide bridge.

22 Claims, 9 Drawing Sheets
Specification includes a Sequence Listing.

A

B

C

A    B

A    B

SEQUENCE LISTING

```
<160> NUMBER OF SEQ ID NOS: 70

<210> SEQ ID NO 1
<211> LENGTH: 11
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: misc_feature
<222> LOCATION: (3)..(3)
<223> OTHER INFORMATION: Xaa = Ser or Gly
<220> FEATURE:
<221> NAME/KEY: misc_feature
<222> LOCATION: (5)..(5)
<223> OTHER INFORMATION: Xaa = Ser or Gly
<220> FEATURE:
<221> NAME/KEY: misc_feature
<222> LOCATION: (6)..(6)
<223> OTHER INFORMATION: Xaa = Ser or Gly
<220> FEATURE:
<221> NAME/KEY: DISULFID
<222> LOCATION: (7)..(10)
<220> FEATURE:
<221> NAME/KEY: misc_feature
<222> LOCATION: (9)..(9)
<223> OTHER INFORMATION: Xaa = Arg-Ser or Val-Ser or Val-Thr

<400> SEQUENCE: 1

Trp Ser Xaa Trp Xaa Xaa Cys Ser Xaa Cys Gly
1               5                   10

<210> SEQ ID NO 2
<211> LENGTH: 12
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (7)..(11)

<400> SEQUENCE: 2

Trp Ser Gly Trp Ser Ser Cys Ser Arg Ser Cys Gly
1               5                   10

<210> SEQ ID NO 3
<211> LENGTH: 13
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: misc_feature
<222> LOCATION: (1)..(1)
<223> OTHER INFORMATION: Xaa = a hydrogen atom or Pro or Ala-Pro or
      Leu-Ala-Pro or Val-Leu-Ala-Pro
<220> FEATURE:
<221> NAME/KEY: misc_feature
<222> LOCATION: (4)..(4)
<223> OTHER INFORMATION: Xaa = Ser or Gly
<220> FEATURE:
<221> NAME/KEY: misc_feature
<222> LOCATION: (6)..(6)
<223> OTHER INFORMATION: Xaa = Ser or Gly
<220> FEATURE:
<221> NAME/KEY: misc_feature
<222> LOCATION: (7)..(7)
<223> OTHER INFORMATION: Xaa = Ser or Gly
<220> FEATURE:
<221> NAME/KEY: DISULFID
<222> LOCATION: (8)..(11)
<220> FEATURE:
<221> NAME/KEY: misc_feature
```

```
<222> LOCATION: (10)..(10)
<223> OTHER INFORMATION: Xaa = Arg-Ser or Val-Ser or Val-Thr
<220> FEATURE:
<221> NAME/KEY: misc_feature
<222> LOCATION: (13)..(13)
<223> OTHER INFORMATION: Xaa = a hydrogen atom or Leu or Leu-Gly or
      Leu-Gly-Leu or Leu-Gly-Leu-Ile or Leu-Gly-Leu-Ile-Phe

<400> SEQUENCE: 3

Xaa Trp Ser Xaa Trp Xaa Xaa Cys Ser Xaa Cys Gly Xaa
1               5                   10

<210> SEQ ID NO 4
<211> LENGTH: 12
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (7)..(11)

<400> SEQUENCE: 4

Trp Ser Ser Trp Ser Ser Cys Ser Arg Ser Cys Gly
1               5                   10

<210> SEQ ID NO 5
<211> LENGTH: 12
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (7)..(11)

<400> SEQUENCE: 5

Trp Ser Ser Trp Ser Gly Cys Ser Arg Ser Cys Gly
1               5                   10

<210> SEQ ID NO 6
<211> LENGTH: 12
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (7)..(11)

<400> SEQUENCE: 6

Trp Ser Ser Trp Gly Ser Cys Ser Arg Ser Cys Gly
1               5                   10

<210> SEQ ID NO 7
<211> LENGTH: 12
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (7)..(11)

<400> SEQUENCE: 7

Trp Ser Ser Trp Gly Gly Cys Ser Arg Ser Cys Gly
1               5                   10

<210> SEQ ID NO 8
```

```
<211> LENGTH: 13
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: MISC_FEATURE
<222> LOCATION: (1)..(1)
<223> OTHER INFORMATION: Xaa = a hydrogen atom or an amino acid chain
      with 0 to 4 amino acids
<220> FEATURE:
<221> NAME/KEY: MISC_FEATURE
<222> LOCATION: (4)..(4)
<223> OTHER INFORMATION: Xaa = Ser or Gly
<220> FEATURE:
<221> NAME/KEY: MISC_FEATURE
<222> LOCATION: (6)..(6)
<223> OTHER INFORMATION: Xaa = Ser or Gly
<220> FEATURE:
<221> NAME/KEY: MISC_FEATURE
<222> LOCATION: (7)..(7)
<223> OTHER INFORMATION: Xaa = Ser or Gly
<220> FEATURE:
<221> NAME/KEY: DISULFID
<222> LOCATION: (8)..(11)
<220> FEATURE:
<221> NAME/KEY: MISC_FEATURE
<222> LOCATION: (10)..(10)
<223> OTHER INFORMATION: Xaa = Arg-Ser or Val-Ser or Val-Thr
<220> FEATURE:
<221> NAME/KEY: MISC_FEATURE
<222> LOCATION: (13)..(13)
<223> OTHER INFORMATION: Xaa = a hydrogen atom or an amino acid chain
      with 0 to 5 amino acids

<400> SEQUENCE: 8

Xaa Trp Ser Xaa Trp Xaa Xaa Cys Ser Xaa Cys Gly Xaa
1               5                   10

<210> SEQ ID NO 9
<211> LENGTH: 12
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (7)..(11)

<400> SEQUENCE: 9

Trp Ser Gly Trp Ser Gly Cys Ser Arg Ser Cys Gly
1               5                   10

<210> SEQ ID NO 10
<211> LENGTH: 12
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (7)..(11)

<400> SEQUENCE: 10

Trp Ser Gly Trp Gly Ser Cys Ser Arg Ser Cys Gly
1               5                   10

<210> SEQ ID NO 11
<211> LENGTH: 12
<212> TYPE: PRT
<213> ORGANISM: Artificial sequence
<220> FEATURE:
<223> OTHER INFORMATION: fragment of the human SCO-spondin
```

```
<220> FEATURE:
<221> NAME/KEY: DISULFID
<222> LOCATION: (7)..(11)

<400> SEQUENCE: 11

Trp Ser Gly Trp Gly Gly Cys Ser Arg Ser Cys Gly
1               5                   10

<210> SEQ ID NO 12
<211> LENGTH: 12
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (7)..(11)

<400> SEQUENCE: 12

Trp Ser Ser Trp Ser Ser Cys Ser Val Ser Cys Gly
1               5                   10

<210> SEQ ID NO 13
<211> LENGTH: 12
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (7)..(11)

<400> SEQUENCE: 13

Trp Ser Ser Trp Ser Gly Cys Ser Val Ser Cys Gly
1               5                   10

<210> SEQ ID NO 14
<211> LENGTH: 12
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (7)..(11)

<400> SEQUENCE: 14

Trp Ser Ser Trp Gly Ser Cys Ser Val Ser Cys Gly
1               5                   10

<210> SEQ ID NO 15
<211> LENGTH: 12
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (7)..(11)

<400> SEQUENCE: 15

Trp Ser Ser Trp Gly Gly Cys Ser Val Ser Cys Gly
1               5                   10

<210> SEQ ID NO 16
<211> LENGTH: 12
<212> TYPE: PRT
<213> ORGANISM: Artificial sequence
<220> FEATURE:
```

```
<223> OTHER INFORMATION: fragment of the human SCO-spondin
<220> FEATURE:
<221> NAME/KEY: DISULFID
<222> LOCATION: (7)..(11)

<400> SEQUENCE: 16

Trp Ser Gly Trp Ser Ser Cys Ser Val Ser Cys Gly
1               5                   10

<210> SEQ ID NO 17
<211> LENGTH: 12
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (7)..(11)

<400> SEQUENCE: 17

Trp Ser Gly Trp Ser Gly Cys Ser Val Ser Cys Gly
1               5                   10

<210> SEQ ID NO 18
<211> LENGTH: 12
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (7)..(11)

<400> SEQUENCE: 18

Trp Ser Gly Trp Gly Ser Cys Ser Val Ser Cys Gly
1               5                   10

<210> SEQ ID NO 19
<211> LENGTH: 12
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (7)..(11)

<400> SEQUENCE: 19

Trp Ser Gly Trp Gly Gly Cys Ser Val Ser Cys Gly
1               5                   10

<210> SEQ ID NO 20
<211> LENGTH: 12
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (7)..(11)

<400> SEQUENCE: 20

Trp Ser Ser Trp Ser Ser Cys Ser Val Thr Cys Gly
1               5                   10

<210> SEQ ID NO 21
<211> LENGTH: 12
<212> TYPE: PRT
<213> ORGANISM: Artificial sequence
```

```
<220> FEATURE:
<223> OTHER INFORMATION: fragment of the human SCO-spondin
<220> FEATURE:
<221> NAME/KEY: DISULFID
<222> LOCATION: (7)..(11)

<400> SEQUENCE: 21

Trp Ser Ser Trp Ser Gly Cys Ser Val Thr Cys Gly
1               5                   10

<210> SEQ ID NO 22
<211> LENGTH: 12
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (7)..(11)

<400> SEQUENCE: 22

Trp Ser Ser Trp Gly Ser Cys Ser Val Thr Cys Gly
1               5                   10

<210> SEQ ID NO 23
<211> LENGTH: 12
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (7)..(11)

<400> SEQUENCE: 23

Trp Ser Ser Trp Gly Gly Cys Ser Val Thr Cys Gly
1               5                   10

<210> SEQ ID NO 24
<211> LENGTH: 12
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (7)..(11)

<400> SEQUENCE: 24

Trp Ser Gly Trp Ser Ser Cys Ser Val Thr Cys Gly
1               5                   10

<210> SEQ ID NO 25
<211> LENGTH: 12
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (7)..(11)

<400> SEQUENCE: 25

Trp Ser Gly Trp Ser Gly Cys Ser Val Thr Cys Gly
1               5                   10

<210> SEQ ID NO 26
<211> LENGTH: 12
<212> TYPE: PRT
```

```
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (7)..(11)

<400> SEQUENCE: 26

Trp Ser Gly Trp Gly Ser Cys Ser Val Thr Cys Gly
1               5                   10

<210> SEQ ID NO 27
<211> LENGTH: 12
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (7)..(11)

<400> SEQUENCE: 27

Trp Ser Gly Trp Gly Gly Cys Ser Val Thr Cys Gly
1               5                   10

<210> SEQ ID NO 28
<211> LENGTH: 13
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (8)..(12)

<400> SEQUENCE: 28

Pro Trp Ser Gly Trp Ser Ser Cys Ser Arg Ser Cys Gly
1               5                   10

<210> SEQ ID NO 29
<211> LENGTH: 14
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (9)..(13)

<400> SEQUENCE: 29

Ala Pro Trp Ser Gly Trp Ser Ser Cys Ser Arg Ser Cys Gly
1               5                   10

<210> SEQ ID NO 30
<211> LENGTH: 15
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (10)..(14)

<400> SEQUENCE: 30

Leu Ala Pro Trp Ser Gly Trp Ser Ser Cys Ser Arg Ser Cys Gly
1               5                   10                  15

<210> SEQ ID NO 31
<211> LENGTH: 16
```

```
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (11)..(15)

<400> SEQUENCE: 31

Val Leu Ala Pro Trp Ser Gly Trp Ser Ser Cys Ser Arg Ser Cys Gly
1               5                   10                  15

<210> SEQ ID NO 32
<211> LENGTH: 13
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (7)..(11)

<400> SEQUENCE: 32

Trp Ser Gly Trp Ser Ser Cys Ser Arg Ser Cys Gly Leu
1               5                   10

<210> SEQ ID NO 33
<211> LENGTH: 14
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (7)..(11)

<400> SEQUENCE: 33

Trp Ser Gly Trp Ser Ser Cys Ser Arg Ser Cys Gly Leu Gly
1               5                   10

<210> SEQ ID NO 34
<211> LENGTH: 15
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (7)..(11)

<400> SEQUENCE: 34

Trp Ser Gly Trp Ser Ser Cys Ser Arg Ser Cys Gly Leu Gly Leu
1               5                   10                  15

<210> SEQ ID NO 35
<211> LENGTH: 16
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (7)..(11)

<400> SEQUENCE: 35

Trp Ser Gly Trp Ser Ser Cys Ser Arg Ser Cys Gly Leu Gly Leu Ile
1               5                   10                  15

<210> SEQ ID NO 36
```

```
<211> LENGTH: 17
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (7)..(11)

<400> SEQUENCE: 36

Trp Ser Gly Trp Ser Ser Cys Ser Arg Ser Cys Gly Leu Gly Leu Ile
1               5                   10                  15

Phe

<210> SEQ ID NO 37
<211> LENGTH: 14
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (8)..(12)

<400> SEQUENCE: 37

Pro Trp Ser Gly Trp Ser Ser Cys Ser Arg Ser Cys Gly Leu
1               5                   10

<210> SEQ ID NO 38
<211> LENGTH: 15
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (8)..(12)

<400> SEQUENCE: 38

Pro Trp Ser Gly Trp Ser Ser Cys Ser Arg Ser Cys Gly Leu Gly
1               5                   10                  15

<210> SEQ ID NO 39
<211> LENGTH: 16
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (8)..(12)

<400> SEQUENCE: 39

Pro Trp Ser Gly Trp Ser Ser Cys Ser Arg Ser Cys Gly Leu Gly Leu
1               5                   10                  15

<210> SEQ ID NO 40
<211> LENGTH: 17
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (8)..(12)

<400> SEQUENCE: 40

Pro Trp Ser Gly Trp Ser Ser Cys Ser Arg Ser Cys Gly Leu Gly Leu
1               5                   10                  15
```

Ile

<210> SEQ ID NO 41
<211> LENGTH: 18
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (8)..(12)

<400> SEQUENCE: 41

Pro Trp Ser Gly Trp Ser Ser Cys Ser Arg Ser Cys Gly Leu Gly Leu
1               5                   10                  15

Ile Phe

<210> SEQ ID NO 42
<211> LENGTH: 15
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (9)..(13)

<400> SEQUENCE: 42

Ala Pro Trp Ser Gly Trp Ser Ser Cys Ser Arg Ser Cys Gly Leu
1               5                   10                  15

<210> SEQ ID NO 43
<211> LENGTH: 16
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (9)..(13)

<400> SEQUENCE: 43

Ala Pro Trp Ser Gly Trp Ser Ser Cys Ser Arg Ser Cys Gly Leu Gly
1               5                   10                  15

<210> SEQ ID NO 44
<211> LENGTH: 17
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (9)..(13)

<400> SEQUENCE: 44

Ala Pro Trp Ser Gly Trp Ser Ser Cys Ser Arg Ser Cys Gly Leu Gly
1               5                   10                  15

Leu

<210> SEQ ID NO 45
<211> LENGTH: 18
<212> TYPE: PRT
<213> ORGANISM: Artificial sequence
<220> FEATURE:
<223> OTHER INFORMATION: fragment of the human SCO-spondin
<220> FEATURE:

```
<221> NAME/KEY: DISULFID
<222> LOCATION: (9)..(13)

<400> SEQUENCE: 45

Ala Pro Trp Ser Gly Trp Ser Ser Cys Ser Arg Ser Cys Gly Leu Gly
1               5                   10                  15

Leu Ile

<210> SEQ ID NO 46
<211> LENGTH: 19
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (9)..(13)

<400> SEQUENCE: 46

Ala Pro Trp Ser Gly Trp Ser Ser Cys Ser Arg Ser Cys Gly Leu Gly
1               5                   10                  15

Leu Ile Phe

<210> SEQ ID NO 47
<211> LENGTH: 16
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (10)..(14)

<400> SEQUENCE: 47

Leu Ala Pro Trp Ser Gly Trp Ser Ser Cys Ser Arg Ser Cys Gly Leu
1               5                   10                  15

<210> SEQ ID NO 48
<211> LENGTH: 17
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (10)..(14)

<400> SEQUENCE: 48

Leu Ala Pro Trp Ser Gly Trp Ser Ser Cys Ser Arg Ser Cys Gly Leu
1               5                   10                  15

Gly

<210> SEQ ID NO 49
<211> LENGTH: 18
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (10)..(14)

<400> SEQUENCE: 49

Leu Ala Pro Trp Ser Gly Trp Ser Ser Cys Ser Arg Ser Cys Gly Leu
1               5                   10                  15

Gly Leu
```

<210> SEQ ID NO 50
<211> LENGTH: 19
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (10)..(14)

<400> SEQUENCE: 50

Leu Ala Pro Trp Ser Gly Trp Ser Ser Cys Ser Arg Ser Cys Gly Leu
1               5                   10                  15

Gly Leu Ile

<210> SEQ ID NO 51
<211> LENGTH: 20
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (10)..(14)

<400> SEQUENCE: 51

Leu Ala Pro Trp Ser Gly Trp Ser Ser Cys Ser Arg Ser Cys Gly Leu
1               5                   10                  15

Gly Leu Ile Phe
            20

<210> SEQ ID NO 52
<211> LENGTH: 17
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (11)..(15)

<400> SEQUENCE: 52

Val Leu Ala Pro Trp Ser Gly Trp Ser Ser Cys Ser Arg Ser Cys Gly
1               5                   10                  15

Leu

<210> SEQ ID NO 53
<211> LENGTH: 18
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (11)..(15)

<400> SEQUENCE: 53

Val Leu Ala Pro Trp Ser Gly Trp Ser Ser Cys Ser Arg Ser Cys Gly
1               5                   10                  15

Leu Gly

<210> SEQ ID NO 54
<211> LENGTH: 19
<212> TYPE: PRT
<213> ORGANISM: Artificial sequence

```
<220> FEATURE:
<223> OTHER INFORMATION: fragment of the human SCO-spondin
<220> FEATURE:
<221> NAME/KEY: DISULFID
<222> LOCATION: (11)..(15)

<400> SEQUENCE: 54

Val Leu Ala Pro Trp Ser Gly Trp Ser Ser Cys Ser Arg Ser Cys Gly
1               5                   10                  15

Leu Gly Leu

<210> SEQ ID NO 55
<211> LENGTH: 20
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (11)..(15)

<400> SEQUENCE: 55

Val Leu Ala Pro Trp Ser Gly Trp Ser Ser Cys Ser Arg Ser Cys Gly
1               5                   10                  15

Leu Gly Leu Ile
            20

<210> SEQ ID NO 56
<211> LENGTH: 21
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (11)..(15)

<400> SEQUENCE: 56

Val Leu Ala Pro Trp Ser Gly Trp Ser Ser Cys Ser Arg Ser Cys Gly
1               5                   10                  15

Leu Gly Leu Ile Phe
            20

<210> SEQ ID NO 57
<211> LENGTH: 11
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa = Ser or Gly
<220> FEATURE:
<221> NAME/KEY: misc_feature
<222> LOCATION: (5)..(5)
<223> OTHER INFORMATION: Xaa = Ser or Gly
<220> FEATURE:
<221> NAME/KEY: misc_feature
<222> LOCATION: (6)..(6)
<223> OTHER INFORMATION: Xaa = Ser or Gly
<220> FEATURE:
<221> NAME/KEY: misc_feature
<222> LOCATION: (9)..(9)
<223> OTHER INFORMATION: Xaa = Arg-Ser or Val-Ser or Val-Thr

<400> SEQUENCE: 57

Trp Ser Xaa Trp Xaa Xaa Cys Ser Xaa Cys Gly
1               5                   10
```

-continued

```
<210> SEQ ID NO 58
<211> LENGTH: 12
<212> TYPE: PRT
<213> ORGANISM: Homo sapiens

<400> SEQUENCE: 58

Trp Ser Gly Trp Ser Ser Cys Ser Arg Ser Cys Gly
1               5                   10

<210> SEQ ID NO 59
<211> LENGTH: 11
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: MISC_FEATURE
<222> LOCATION: (3)..(3)
<223> OTHER INFORMATION: Xaa = Ser or Gly
<220> FEATURE:
<221> NAME/KEY: MISC_FEATURE
<222> LOCATION: (5)..(5)
<223> OTHER INFORMATION: Xaa = Ser or Gly
<220> FEATURE:
<221> NAME/KEY: MISC_FEATURE
<222> LOCATION: (6)..(6)
<223> OTHER INFORMATION: Xaa = Ser or Gly
<220> FEATURE:
<221> NAME/KEY: DISULFID
<222> LOCATION: (7)..(10)
<220> FEATURE:
<221> NAME/KEY: MISC_FEATURE
<222> LOCATION: (9)..(9)
<223> OTHER INFORMATION: Xaa = Arg-Ser or Val-Ser or Val-Thr or Arg-Thr

<400> SEQUENCE: 59

Trp Ser Xaa Trp Xaa Xaa Cys Ser Xaa Cys Gly
1               5                   10

<210> SEQ ID NO 60
<211> LENGTH: 12
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (7)..(11)

<400> SEQUENCE: 60

Trp Ser Ser Trp Ser Ser Cys Ser Arg Thr Cys Gly
1               5                   10

<210> SEQ ID NO 61
<211> LENGTH: 12
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (7)..(11)

<400> SEQUENCE: 61

Trp Ser Ser Trp Ser Gly Cys Ser Arg Thr Cys Gly
1               5                   10

<210> SEQ ID NO 62
<211> LENGTH: 12
<212> TYPE: PRT
<213> ORGANISM: Artificial sequence
```

```
<220> FEATURE:
<223> OTHER INFORMATION: fragment of the human SCO-spondin
<220> FEATURE:
<221> NAME/KEY: DISULFID
<222> LOCATION: (7)..(11)

<400> SEQUENCE: 62

Trp Ser Ser Trp Gly Ser Cys Ser Arg Thr Cys Gly
1               5                   10

<210> SEQ ID NO 63
<211> LENGTH: 12
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (7)..(11)

<400> SEQUENCE: 63

Trp Ser Ser Trp Gly Gly Cys Ser Arg Thr Cys Gly
1               5                   10

<210> SEQ ID NO 64
<211> LENGTH: 12
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (7)..(11)

<400> SEQUENCE: 64

Trp Ser Gly Trp Ser Ser Cys Ser Arg Thr Cys Gly
1               5                   10

<210> SEQ ID NO 65
<211> LENGTH: 12
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (7)..(11)

<400> SEQUENCE: 65

Trp Ser Gly Trp Ser Gly Cys Ser Arg Thr Cys Gly
1               5                   10

<210> SEQ ID NO 66
<211> LENGTH: 12
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (7)..(11)

<400> SEQUENCE: 66

Trp Ser Gly Trp Gly Ser Cys Ser Arg Thr Cys Gly
1               5                   10

<210> SEQ ID NO 67
<211> LENGTH: 12
<212> TYPE: PRT
```

```
<213> ORGANISM: Artificial sequence
<220> FEATURE:
<223> OTHER INFORMATION: fragment of the human SCO-spondin
<220> FEATURE:
<221> NAME/KEY: DISULFID
<222> LOCATION: (7)..(11)

<400> SEQUENCE: 67

Trp Ser Gly Trp Gly Gly Cys Ser Arg Thr Cys Gly
1               5                   10

<210> SEQ ID NO 68
<211> LENGTH: 13
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: MISC_FEATURE
<222> LOCATION: (1)..(1)
<223> OTHER INFORMATION: Xaa = a hydrogen atom or an amino acid chain
      with 0 to 4 amino acids
<220> FEATURE:
<221> NAME/KEY: MISC_FEATURE
<222> LOCATION: (4)..(4)
<223> OTHER INFORMATION: Xaa = Ser or Gly
<220> FEATURE:
<221> NAME/KEY: MISC_FEATURE
<222> LOCATION: (6)..(6)
<223> OTHER INFORMATION: Xaa = Ser or Gly
<220> FEATURE:
<221> NAME/KEY: MISC_FEATURE
<222> LOCATION: (7)..(7)
<223> OTHER INFORMATION: Xaa = Ser or Gly
<220> FEATURE:
<221> NAME/KEY: DISULFID
<222> LOCATION: (8)..(11)
<220> FEATURE:
<221> NAME/KEY: MISC_FEATURE
<222> LOCATION: (10)..(10)
<223> OTHER INFORMATION: Xaa = Arg-Ser or Val-Ser or Val-Thr or Arg-Thr
<220> FEATURE:
<221> NAME/KEY: MISC_FEATURE
<222> LOCATION: (13)..(13)
<223> OTHER INFORMATION: Xaa = a hydrogen atom or an amino acid chain
      with 0 to 5 amino acids

<400> SEQUENCE: 68

Xaa Trp Ser Xaa Trp Xaa Xaa Cys Ser Xaa Cys Gly Xaa
1               5                   10

<210> SEQ ID NO 69
<211> LENGTH: 13
<212> TYPE: PRT
<213> ORGANISM: Artificial sequence
<220> FEATURE:
<223> OTHER INFORMATION: fragment of the human SCO-spondin
<220> FEATURE:
<221> NAME/KEY: MISC_FEATURE
<222> LOCATION: (1)..(1)
<223> OTHER INFORMATION: Xaa = a hydrogen atom or Pro or Ala-Pro or
      Leu-Ala-Pro or Val-Leu-Ala-Pro
<220> FEATURE:
<221> NAME/KEY: MISC_FEATURE
<222> LOCATION: (4)..(4)
<223> OTHER INFORMATION: Xaa = Ser or Gly
<220> FEATURE:
<221> NAME/KEY: MISC_FEATURE
<222> LOCATION: (6)..(6)
<223> OTHER INFORMATION: Xaa = Ser or Gly
<220> FEATURE:
<221> NAME/KEY: MISC_FEATURE
<222> LOCATION: (7)..(7)
<223> OTHER INFORMATION: Xaa = Ser or Gly
<220> FEATURE:
```

```
<221> NAME/KEY: DISULFID
<222> LOCATION: (8)..(11)
<220> FEATURE:
<221> NAME/KEY: MISC_FEATURE
<222> LOCATION: (10)..(10)
<223> OTHER INFORMATION: Xaa = Arg-Ser or Val-Ser or Val-Thr or Arg-Thr
<220> FEATURE:
<221> NAME/KEY: MISC_FEATURE
<222> LOCATION: (13)..(13)
<223> OTHER INFORMATION: Xaa = a hydrogen atom or Leu or Leu-Gly or
      Leu-Gly-Leu or Leu-Gly-Leu-Ile or Leu-Gly-Leu-Ile-Phe

<400> SEQUENCE: 69

Xaa Trp Ser Xaa Trp Xaa Xaa Cys Ser Xaa Cys Gly Xaa
1               5                   10

<210> SEQ ID NO 70
<211> LENGTH: 11
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa = Ser or Gly
<220> FEATURE:
<221> NAME/KEY: MISC_FEATURE
<222> LOCATION: (5)..(5)
<223> OTHER INFORMATION: Xaa = Ser or Gly
<220> FEATURE:
<221> NAME/KEY: MISC_FEATURE
<222> LOCATION: (6)..(6)
<223> OTHER INFORMATION: Xaa = Ser or Gly
<220> FEATURE:
<221> NAME/KEY: MISC_FEATURE
<222> LOCATION: (9)..(9)
<223> OTHER INFORMATION: Xaa = Arg-Ser or Val-Ser or Val-Thr or Arg-Thr

<400> SEQUENCE: 70

Trp Ser Xaa Trp Xaa Xaa Cys Ser Xaa Cys Gly
1               5                   10
```

CYCLIC POLYPEPTIDES, METHOD FOR OBTAINING THEM AND THE THERAPEUTIC USE THEREOF

FIELD OF THE INVENTION

The invention relates to novel cyclic polypeptides, the pharmaceutical compositions comprising them, and their use as medicaments, in particular their use in the treatment of neurodegenerative diseases and the regeneration of the cells of the central and peripheral nervous system, and the method of obtaining of these cyclic polypeptides.

BACKGROUND OF THE INVENTION

The polypeptides of the invention have an amino acid sequence derived from one of the conserved consensus domains of SCO-spondin called thrombospondin type 1 repeat or TSR.

It is well known that different synthetic peptides deduced from the structure of thrombospondin have interesting effects on different cell types, in particular they inhibit tumors in mammals, influence thrombolysis and angiogenesis and may be complementary modulators or even ensure the promotion of cell attachment [Sipes J M et al., J Cell Biol, 121, 469-77, 1993; Rusnati M et al. Pharmaceuticals 3, 1241-1278, 2010; Lopez-Dee Z et al., Mediators of Inflammation, Volume 2011, Article ID 296069, 10 pages, 201i].

The general characteristics of SCO-spondin are described in particular in the article by Meiniel et al., Microsc Res Tech. 2, 484-95, 2001 and the article by Gobron et al. Glia 32, 177-91, 2000.

The application of an amino acid sequence polypeptide: W-S-G-W-S-S-C-S-R-S-C-G, [SEQ ID NO: 58] corresponding to the most representative amino acid sequence of one of the SCO-spondin TSR motifs, leads in the B104 cells from rat neuroblastoma a cell differentiation inducing neuritic growth and cell aggregation [F. El-Bitar et al., Cell Tissue Res., Vol. 304, p. 361-369.2001]. This polypeptide does not have a disulfide bridge between the two cysteines.

This polypeptide as well as the reduced form polypeptides of formula SEQ ID NO: 70 and, in particular, of formula SEQ ID NO: 57 are described and claimed in international patent applications WO 1999/03890 (corresponding to U.S. Pat. No. 6,995,140) and WO2009027350, or may be prepared based on the description of these patents and methods known to those skilled in the art.

However, the stability of the polypeptide W-S-G-W-S-S-C-S-R-S-C-G [SEQ ID NO: 58] decreases in aqueous solution over time. It would therefore be necessary for this polypeptide to be prepared extemporaneously during the treatments, which could complicate the administration thereof, thus limiting the possibilities of carrying out treatments by direct injection, or, for example, by means of pumps for the progressive delivery of the medicament to the patients. In general, this low stability would present a certain disadvantage for the development of therapeutic concepts based on this polypeptide.

Patent application WO 2008/090285 discloses peptidomimetic analogs of the polypeptide W-S-G-W-S-S-C-S-R-S-C-G [SEQ ID NO: 58]. This approach, however, has two disadvantages: these polypeptides contain non-natural amino acids that are likely to cause immunogenicity phenomena, and a significant increase in production costs, while non-natural amino acids are much more expensive than natural amino acids, which diminishes their commercial interest.

SUMMARY OF THE INVENTION

One of the aims of the invention is to provide peptide compounds that are stable and soluble in solutions compatible, in particular, with intrathecal administrations while preserving or improving the properties of the polypeptides of formula SEQ ID NO: 70 and, in particular, the polypeptides of formula SEQ ID NO: 57, particularly the polypeptide of sequence W-S-G-W-S-S-C-S-R-S-C-G [SEQ ID NO: 58].

It is, in fact, particularly important for some desired clinical indications to develop a more soluble form of the polypeptide of amino acid sequence W-S-G-W-S-S-C-S-R-S-C-G [SEQ ID NO: 58] described in international patent application WO 1999/03890.

In fact, for intrathecal injections (IT), the choice of solutions used to administer the compound is very limited. In practice, there are only three solutions used, physiological fluid, artificial cerebrospinal fluid and 5% glucose solutions. Other solutions known to those skilled in the art may be used if other means of administration such as the intraventricular, epidural, intraspinal, intraparenchymal, intravenous, intraluminal, intravitreal, transphenoidal or topical routes are used. Moreover, pharmaceutical compositions may be produced in any form, in particular liquid, in particular injectable preparations in the form of solutions, suspensions or emulsions, infusion preparations, or solid, and include any type of support, in particular gels, biopolymers or biomaterials or any medical device, such as implants or implantable pumps for example, allowing a controlled release or a vectorization system.

Aqueous solutions may be prepared using various solvents that are compatible with the administration route, ideally an isotonic solvent such as 0.9% sodium chloride or 5% glucose, but the solvent may also be water, saline solution, phosphate buffers, citrate or acetate or any other. Optionally, the preparation may also contain, in combination or not, any excipient, adjuvant or additive such as propylene glycol, glycerol, polyethylene glycol or any surfactant, wetting, viscosifying, chelating, isotonizing, antioxidant or stabilizing agent.

Preparations in the form of solutions may be administered by bolus injection or by infusion.

DETAILED DESCRIPTION OF THE INVENTION

In the case of the polypeptide of amino acid sequence: W-S-G-W-S-S-C-S-R-S-C-G, [SEQ ID NO: 58], the solubility in the physiological liquid is low, i.e. of the order of 1-2 mg/ml, and therefore makes it more difficult to obtain the maximum desired clinical doses that are of the order of 10 mg/ml. Solubility is particularly important for IT injections because there is a limitation of the injection volume, a limit which is much greater than that for peripheral injections, and a limitation in the solvents and solutions that may be used, for example. The use of a 5% glucose solution improves the solubility of the polypeptide of amino acid sequence: W-S-G-W-S-S-C-S-R-S-C-G [SEQ ID NO: 58] by bringing it to around 10 mg/ml, wherein this solution remains an isotonic solution that is compatible with an IT injection.

However, the presence of glucose in contact with the polypeptide is known to form Schiff bases, as a result of the reaction of the aldehyde form of glucose with the primary amines of the polypeptides according to the reaction scheme:

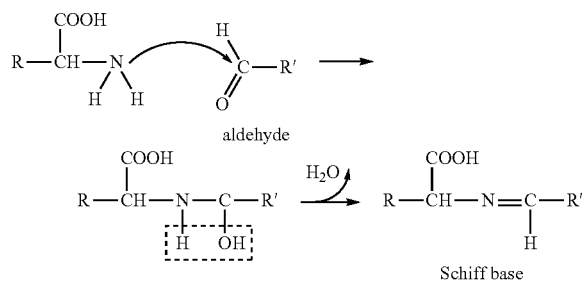

Theoretically, these Schiff bases could complicate the preparation and implementation of the pharmaceutical compositions. However, in the case of the present polypeptides, these bases are reversible in vivo.

It is therefore very important to develop a more soluble form of the polypeptide of amino acid sequence: W-S-G-W-S-S-C-S-R-S-C-G [SEQ ID NO: 58] in a solvent other than 5% glucose and preferably in physiological fluid or artificial cerebrospinal fluid.

Another aspect of the invention is to provide peptide compounds that are effective in the treatment of neurodegenerative diseases or nerve trauma in which the regeneration of nerve cells is required, as well as pharmaceutical compositions comprising them.

Another aspect of the invention is to provide a method to obtain these peptide compounds.

The present invention provides a polypeptide comprising the following amino acid sequence:

```
                                (SEQ ID NO: 59)
W-S-X1-W-X2-X3-C-S-X4-C-G
``` in which:

X1, X2 and X3 represent S or G independently of one another,

X4 represents R-S or V-S or V-T or R-T, and the two cysteines form a disulfide bridge.

The present invention relates, in particular, to a polypeptide comprising the following amino acid sequence:

```
                                (SEQ ID NO: 59)
W-S-X1-W-X2-X3-C-S-X4-C-G
``` in which:

X1, X2 and X3 represent S or G independently of one another,

X4 represents R-S or V-S or V-T or R-T, and the two cysteines form a disulfide bridge, wherein the polypeptide is substantially free of the reduced or dimeric or oligomeric forms of the polypeptide, as well as derivatives of the polypeptide in which the thiol groups are in the sulfoxide or sulfone form.

In the sequence SEQ ID NO: 59 above, X4 represents R-S or V-S or V-T or R-T. In another preferred embodiment of the invention, X4 may also represent R-S or V-S or V-T.

The object of the invention is, therefore, also a polypeptide as described above comprising the following amino acid sequence:

```
                                (SEQ ID NO: 1)
W-S-X1-W-X2-X3-C-S-X4-C-G
``` in which:

X1, X2 and X3 have the meaning indicated above, and

X4 represents R-S or V-S or V-T, and the two cysteines form a disulfide bridge.

For the purposes of the present invention, the term "amino acids" means both natural amino acids and non-natural amino acids.

By "natural amino acids" is meant the amino acids in L form that may be found in natural proteins, i.e. alanine, arginine, asparagine, aspartic acid, cysteine; glutamine, glutamic acid, glycine, histidine, isoleucine, leucine, lysine, methionine, phenylalanine, proline, serine, threonine, tryptophan, tyrosine and valine.

By "non-natural amino acid" is meant the preceding amino acids in their D form, as well as the homo forms of certain amino acids such as arginine, lysine, phenylalanine and serine, or the nor forms of leucine or valine.

This definition also comprises other amino acids such as alphaaminobutyric acid, agmatine, alpha-aminoisobutyric acid, sarcosine, statin, ornithine, deaminotyrosine.

The nomenclature used to describe the peptide sequences is the international nomenclature using the one-letter code and where the amino-terminal end is shown on the left and the carboxy-terminus is shown on the right.

The dashes "-" represent common peptide bonds linking the amino acids of the sequences.

For the purposes of the present invention, the term "polypeptide" is intended to mean any polymer of amino acids linked to one another by peptide bonds, irrespective of its length. Thus, for the purposes of the present invention, the term polypeptide also encompasses peptides and proteins.

The present invention relates to a polypeptide comprising the following amino acid sequence:

```
                                (SEQ ID NO: 59)
W-S-X1-W-X2-X3-C-S-X4-C-G
``` in which:

X1, X2 and X3 represent S or G independently of one another,

X4 represents R-S or V-S or V-T or R-T, and the two cysteines form a disulfide bridge.

The product SEQ ID NO: 59 therefore has the structure:

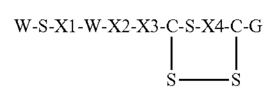

In this embodiment, the invention relates to polypeptides comprising the following amino acid sequences:

```
                           SEQ ID NO: 4
W-S-S-W-S-S-C-S-R-S-C-G

SEQ ID NO: 5
W-S-S-W-S-G-C-S-R-S-C-G

SEQ ID NO: 6
W-S-S-W-G-S-C-S-R-S-C-G

SEQ ID NO: 7
W-S-S-W-G-G-C-S-R-S-C-G
```

W-S-G-W-S-S-C-S-R-S-C-G SEQ ID NO: 2
W-S-G-W-S-G-C-S-R-S-C-G SEQ ID NO: 9
W-S-G-W-G-S-C-S-R-S-C-G SEQ ID NO: 10
W-S-G-W-G-G-C-S-R-S-C-G SEQ ID NO: 11
W-S-S-W-S-S-C-S-V-S-C-G SEQ ID NO: 12
W-S-S-W-S-G-C-S-V-S-C-G SEQ ID NO: 13
W-S-S-W-G-S-C-S-V-S-C-G SEQ ID NO: 14
W-S-S-W-G-G-C-S-V-S-C-G SEQ ID NO: 15
W-S-G-W-S-S-C-S-V-S-C-G SEQ ID NO: 16
W-S-G-W-S-G-C-S-V-S-C-G SEQ ID NO: 17
W-S-G-W-G-S-C-S-V-S-C-G SEQ ID NO: 18
W-S-G-W-G-G-C-S-V-S-C-G SEQ ID NO: 19
W-S-S-W-S-S-C-S-V-T-C-G SEQ ID NO: 20
W-S-S-W-S-G-C-S-V-T-C-G SEQ ID NO: 21
W-S-S-W-G-S-C-S-V-T-C-G SEQ ID NO: 22
W-S-S-W-G-G-C-S-V-T-C-G SEQ ID NO: 23
W-S-G-W-S-S-C-S-V-T-C-G SEQ ID NO: 24
W-S-G-W-S-G-C-S-V-T-C-G SEQ ID NO: 25
W-S-G-W-G-S-C-S-V-T-C-G SEQ ID NO: 26
W-S-G-W-G-G-C-S-V-T-C-G SEQ ID NO: 27
W-S-S-W-S-S-C-S-R-T-C-G SEQ ID NO: 60
W-S-S-W-S-G-C-S-R-T-C-G SEQ ID NO: 61
W-S-S-W-G-S-C-S-R-T-C-G SEQ ID NO: 62
W-S-S-W-G-G-C-S-R-T-C-G SEQ ID NO: 63
W-S-G-W-S-S-C-S-R-T-C-G SEQ ID NO: 64
W-S-G-W-S-G-C-S-R-T-C-G SEQ ID NO: 65
W-S-G-W-G-S-C-S-R-T-C-G SEQ ID NO: 66
W-S-G-W-G-G-C-S-R-T-C-G SEQ ID NO: 67 in which the two cysteines represented in these sequences form between them a disulfide bridge.

According to an advantageous embodiment, the invention relates to a polypeptide as defined above comprising the following amino acid sequence:

W-S-G-W-S-S-C-S-R-S-C-G (SEQ ID NO: 2)

wherein the two cysteines form a disulfide bridge.

The product SEQ ID NO: 2 therefore has the structure;

W-S-G-W-S-S-C-S-R-S-C-G
        |         |
        S————S

Surprisingly, the inventors have found that the formation of a sulfide bridge between the two cysteines present in the amino acid sequence polypeptide W-S-G-W-S-S-C-S-R-S-C-G [SEQ ID NO: 2], allowed not only the preservation of the effectiveness of the polypeptide in inducing an increase in neuritic growth as well as an increase in synaptic contacts, but also the obtaining of a polypeptide having a better stability and a better solubility in solutions that are compatible with administration, particularly intrathecal administration.

This invention is all the more surprising in that, in the SCO-spondin protein from which this peptide sequence is derived, the two cysteines present in the sequence W-S-G-W-S-S-C-S-R-S-C-G [SEQ ID NO: 2] above, do not form a disulfide bridge with each other but instead are involved in disulfide bridges with other cysteines present in the protein.

According to a particular embodiment, the invention relates to a polypeptide as defined above, consisting of the following amino acid sequence:

X7-W-S-X1-W-X2-X3-C-S-X4-C-G-X8 (SEQ ID NO: 68)

in which:
X1, X2 and X3 represent S or G independently of one another,
X4 represents R-S or V-S or V-T or R-T,
the two cysteines form a disulfide bridge,
X7 represents a hydrogen atom or a chain of amino acids having from 0 to 4 amino acids, and
X8 represents a hydrogen atom or a chain of amino acids having from 0 to 5 amino acids.

According to another specific embodiment, the invention relates to a polypeptide as defined above, consisting of the following amino acid sequence:

X5-W-S-X1-W-X2-X3-C-S-X4-C-G-X6 (SEQ ID NO: 69)

in which:
X1, X2 and X3 represent S or G independently of one another,

X4 represents R-S or V-S or V-T or R-T,
the two cysteines form a disulfide bridge,
X5 represents a hydrogen atom or P or A-P or L-A-P or V-L-A-P, and
X6 represents a hydrogen atom or L or L-G or L-G-L or L-G-L-I or L-G-L-I-F.

In the sequences SEQ ID NO: 68 and SEQ ID NO: 69 above, X4 represents R-S or V-S or V-T or R-T.

In another preferred embodiment of the invention, X4 may also represent R-S or V-S or V-T. The corresponding sequences are the sequences SEQ ID NO: 8 and SEQ ID NO: 3.

In this embodiment, the invention relates, in particular, to the polypeptide sequence:

```
                                                  (SEQ ID NO: 2)
                    W-S-G-W-S-S-C-S-R-S-C-G
``` as well as the polypeptides, with the following amino acid sequences:

```
                                                  SEQ ID NO: 28
P-W-S-G-W-S-S-C-S-R-S-C-G

SEQ ID NO: 29
A-P-W-S-G-W-S-S-C-S-R-S-C-G

SEQ ID NO: 30
L-A-P-W-S-G-W-S-S-C-S-R-S-C-G

SEQ ID NO: 31
V-L-A-P-W-S-G-W-S-S-C-S-R-S-C-G

SEQ ID NO: 32
W-S-G-W-S-S-C-S-R-S-C-G-L

SEQ ID NO: 33
W-S-G-W-S-S-C-S-R-S-C-G-L-G

SEQ ID NO: 34
W-S-G-W-S-S-C-S-R-S-C-G-L-G-L

SEQ ID NO: 35
W-S-G-W-S-S-C-S-R-S-C-G-L-G-L-I

SEQ ID NO: 36
W-S-G-W-S-S-C-S-R-S-C-G-L-G-L-I-F

SEQ ID NO: 37
P-W-S-G-W-S-S-C-S-R-S-C-G-L

SEQ ID NO: 38
P-W-S-G-W-S-S-C-S-R-S-C-G-L-G

SEQ ID NO: 39
P-W-S-G-W-S-S-C-S-R-S-C-G-L-G-L

SEQ ID NO: 40
P-W-S-G-W-S-S-C-S-R-S-C-G-L-G-L-I

SEQ ID NO: 41
P-W-S-G-W-S-S-C-S-R-S-C-G-L-G-L-I-F

SEQ ID NO: 42
A-P-W-S-G-W-S-S-C-S-R-S-C-G-L

SEQ ID NO: 43
A-P-W-S-G-W-S-S-C-S-R-S-C-G-L-G

SEQ ID NO: 44
A-P-W-S-G-W-S-S-C-S-R-S-C-G-L-G-L

SEQ ID NO: 45
A-P-W-S-G-W-S-S-C-S-R-S-C-G-L-G-L-I

SEQ ID NO: 46
A-P-W-S-G-W-S-S-C-S-R-S-C-G-L-G-L-I-F

SEQ ID NO: 47
L-A-P-W-S-G-W-S-S-C-S-R-S-C-G-L

SEQ ID NO: 48
L-A-P-W-S-G-W-S-S-C-S-R-S-C-G-L-G

SEQ ID NO: 49
L-A-P-W-S-G-W-S-S-C-S-R-S-C-G-L-G-L

SEQ ID NO: 50
L-A-P-W-S-G-W-S-S-C-S-R-S-C-G-L-G-L-I

SEQ ID NO: 51
L-A-P-W-S-G-W-S-S-C-S-R-S-C-G-L-G-L-I-F

SEQ ID NO: 52
V-L-A-P-W-S-G-W-S-S-C-S-R-S-C-G-L

SEQ ID NO: 53
V-L-A-P-W-S-G-W-S-S-C-S-R-S-C-G-L-G

SEQ ID NO: 54
V-L-A-P-W-S-G-W-S-S-C-S-R-S-C-G-L-G-L

SEQ ID NO: 55
V-L-A-P-W-S-G-W-S-S-C-S-R-S-C-G-L-G-L-I

SEQ ID NO: 56
V-L-A-P-W-S-G-W-S-S-C-S-R-S-C-G-L-G-L-I-F
``` sequences in which both cysteines form a disulfide bridge.

According to an even more advantageous embodiment, the invention relates to a polypeptide as defined above, consisting of the following amino acid sequence:

```
                                                  (SEQ ID NO: 2)
                    W-S-G-W-S-S-C-S-R-S-C-G
``` in which the two cysteines form a disulfide bridge.

According to an advantageous embodiment, the invention relates to a polypeptide as defined above, consisting of the following amino acid sequence:

```
                                                  (SEQ ID NO: 59)
                    W-S-X1-W-X2-X3-C-S-X4-C-G
``` in which:
X1, X2 and X3 represent S or G independently of one another,
X4 represents R-S or V-S or V-T or R-T, and
the two cysteines form a disulfide bridge,
wherein the polypeptide is substantially free of reduced, dimeric or oligomeric forms of the polypeptide as well as derivatives of the polypeptide in which the thiol groups are in the form of sulfoxide or sulfone.

The term "substantially free" means that the polypeptide according to the preferred embodiment indicated above, comprises very small amounts of impurities that the inventors of the present application have identified. These impurities comprise the reduced structure in which the two thiol groups of the two cysteines are in free form, dimers (or polymers) as well as oxidized forms in which the thiol groups are in the form of sulfoxide or sulfone. The obtaining of this practically pure form is preferably carried out by implementing the method described below. Under these conditions, the purity of the product obtained is of the order of 80% minimum. This purity may reach 85, 90 or even 95%.

According to another advantageous embodiment, the invention therefore relates to a polypeptide consisting of the following amino acid sequence:

(SEQ ID NO: 59)
W-S-X1-W-X2-X3-C-S-X4-C-G in which:
X1, X2 and X3 represent S or G independently of one another,
X4 represents R-S or V-S or V-T or R-T, and
the two cysteines form a disulfide bridge,
wherein the polypeptide has a purity greater than 80%, preferably 85%, more preferably 90%, even more preferably equal to or greater than 95%.

According to a more specific embodiment, the invention relates to a polypeptide consisting of the following amino acid sequence:

(SEQ ID NO: 2)
W-S-G-W-S-S-C-S-R-S-C-G in which the two cysteines form a disulfide bridge, wherein the polypeptide is substantially free of reduced or dimeric or oligomeric forms of the polypeptide as well as derivatives of the polypeptide whose thiol groups are in the form of sulfoxide or sulfone.

Conventional purification methods, for example by chromatography, may be used to purify the desired disulfide bridge containing products.

For example, the synthesis of the compound corresponding to the sequence SEQ ID NO: 2 carried out by methods known to those skilled in the art in the absence of albumin, produces a mixture of about 60 products, among which is the desired product with a purity of 44.51% determined by HPLC. Several successive HPLCs using a 0.1% TFA/water/acetonitrile gradient followed by a mixture of the identical fractions (pooling) make it possible to isolate the compound corresponding to the sequence SEQ ID NO: 2 with a final purity of 99%.

According to a still more particular embodiment, the invention therefore relates to a polypeptide as defined above, consisting of the following amino acid sequence:

(SEQ ID NO: 2)
W-S-G-W-S-S-C-S-R-S-C-G in which the two cysteines form a disulfide bridge,
wherein the polypeptide has a purity greater than 80%, preferably 85%, more preferably 90%, even more preferably equal to or greater than 95%.

According to another aspect, the invention relates to a method for obtaining the amino acid sequence polypeptide SEQ ID NO: 59:

(SEQ ID NO: 59)
W-S-X1-W-X2-X3-C-S-X4-C-G in which:
X1, X2 and X3 represent S or G independently of one another,
X4 represents R-S or V-S or V-T or R-T, and
the two cysteines form a disulfide bridge,
comprising a step of forming a disulfide bridge in the presence of albumin in the polypeptide of sequence SEQ ID NO: 70:

(SEQ ID NO: 70)
W-S-X1-W-X2-X3-C-S-X4-C-G in which:
X1, X2 and X3 represent S or G independently of one another,
X4 represents R-S or V-S or V-T or R-T,
wherein the polypeptide of sequence SEQ ID NO: 70 is in solution, preferably in aqueous solution.

The polypeptide sequence SEQ ID NO: 70 does not have a disulfide bridge.

In this embodiment of the invention, the formation of a disulfide bridge between two cysteines of the amino acid sequence is achieved by oxidation of the cysteines.

In the sequence SEQ ID NO: 70 above, X4 represents R-S or V-S or V-T or R-T.

In another preferred embodiment of the invention, it is also possible to implement the above method from the product having the sequence SEQ ID NO: 57 in which X4 represents R-S or V-S or V-T.

According to another aspect, the invention relates to a method for obtaining the polypeptide of amino acid sequence SEQ ID NO: 2:

(SEQ ID NO: 2)
W-S-G-W-S-S-C-S-R-S-C-G in which:
the two cysteines form a disulfide bridge,
comprising a step of forming a disulfide bridge in the presence of albumin in the polypeptide of sequence SEQ ID NO: 58:

(SEQ ID NO: 58)
W-S-G-W-S-S-C-S-R-S-C-G

The inventors of the present application have discovered an inventive and unexpected method of forming a disulfide bridge. This method consists in using albumin as an oxidizing catalyst in order to reduce or avoid the formation of impurities and also to accelerate the kinetic of reaction, a result which is always favorable for the industrial production of peptides.

The presence of albumin in the reaction makes it possible, in particular, to accelerate the oxidation of the starting product. In an oxidation reaction, it is often desirable to gently accelerate the reaction to avoid the creation of undesirable products from uncontrolled oxidation. The results provided in the experimental part show that the reaction in the presence of albumin allows better control of the products formed (more particularly of the polypeptide of sequence SEQ ID NO: 2) and therefore better purity.

More particularly, the invention relates to a method for obtaining the polypeptide of sequence SEQ ID NO: 1 or a polypeptide of sequence SEQ ID NO: 2 as defined above, characterized in that the albumin and the polypeptide of sequence SEQ ID NO: 70 or the polypeptide of sequence SEQ ID NO: 58 are present in an albumin:polypeptide ratio of 1:1 to 1:100, preferably 1:1 to 1:10, and more preferably 1:1.

According to another particular embodiment, the invention relates to a method for obtaining the polypeptide of sequence SEQ ID NO: 59 or the polypeptide of sequence SEQ ID NO: 2 as defined above, characterized in that the step of formation of a disulfide bridge in the presence of albumin in the polypeptide of sequence SEQ ID NO: 70 or the polypeptide of sequence SEQ ID NO: 58 is carried out in ambient air.

According to another particular embodiment, the invention also relates to a method for obtaining the polypeptide of sequence SEQ ID NO: 1 as defined above, characterized in that the step of forming a disulfide bridge in the presence of albumin in the polypeptide of sequence SEQ ID NO: 57 is carried out in ambient air.

According to an advantageous embodiment, the invention relates to a method for obtaining the polypeptide of sequence SEQ ID NO: 59 or the polypeptide of sequence SEQ ID NO: 2 as defined above, characterized in that the step of forming a disulfide bridge in the presence of albumin in the polypeptide of sequence SEQ ID NO: 70 or in the polypeptide of sequence SEQ ID NO: 58 is carried out without detaching the polypeptide of sequence SEQ ID NO: 70 or the polypeptide of sequence SEQ ID NO: 58 from the resin used for the peptide synthesis of these polypeptides, and in that the polypeptide of sequence SEQ ID NO: 59 or the polypeptide of sequence SEQ ID NO: 2 is then obtained by separating the polypeptide from the resin after the step of formation of the disulfide bridge.

It is also possible, under the same conditions, to obtain the polypeptide of sequence SEQ ID NO: 1 from the polypeptide of sequence SEQ ID NO: 57.

The method for preparing the polypeptide of sequence SEQ ID NO: 58 is based on solid phase peptide synthesis using amino acids protected by N-α-Fmoc as synthons for the construction of the polypeptide.

The glycyl residue at the C-terminal position is coupled to the MBHA resin as part of the Fmoc-Gly-MPPA-OH linker. The other amino acid residues are incorporated in a sequence of cycles of Fmoc group deprotection and of coupling of amino acids to produce protected polypeptide linked to the resin. After the solid phase assembly of the polypeptide, a cleavage reaction of the polypeptide of the resin and deprotection of said polypeptide is carried out simultaneously in one step with a trifluoroacetic acid (TFA)/water mixture to produce the crude polypeptide, which is precipitated using an MTBE/hexane mixture, then filtered and dried.

Before purification, the crude polypeptide of sequence SEQ ID NO: 58 is dissolved in an acetonitrile/water/acetic acid (AcOH) mixture. Purification is performed by preparative reverse phase chromatography using first a trifluoroacetic acid (TFA) eluent and then an acetate eluent. The resulting purified polypeptide (as acetate salt) in solution is diluted with water and concentrated. After adding 5% acetonitrile, the solution obtained is filtered and lyophilized to give the polypeptide of sequence SEQ ID NO: 58 in its medicament form.

This method has several advantages. Work carried out directly on resin is better controlled and therefore cleaner. It produces fewer impurities and avoids several intermediate steps (including the complex purification of the polypeptides of SEQ ID NO: 70, or SEQ ID NO: 58, or SEQ ID NO: 57). Optimized experimental conditions in terms of concentration, solvents and incubation times may be determined by those skilled in the art.

The invention also relates to a polypeptide of sequence SEQ ID NO: 59 as obtained by the previously defined method.

The invention also relates to a polypeptide of sequence SEQ ID NO: 1 as obtained by the previously defined method.

The invention also relates to a polypeptide of sequence SEQ ID NO: 2 as obtained by the previously defined method.

In another aspect, the invention relates to a pharmaceutical composition comprising as active ingredient a polypeptide as previously described and optionally one or more pharmaceutically-acceptable excipients.

The peptide compounds according to the invention may be used in a pharmaceutical composition or in the manufacture of a medicament. In these compositions or medicaments, the active principle may be incorporated into compositions in various forms, i.e. in the form of solutions, generally aqueous solutions, or in freeze-dried form, or in the form of a gel or of a hydrogel, or in the form of emulsion or any other pharmaceutically and physiologically-acceptable form.

The doses to be used may range from 1 µg/kg to 1,000 µg/kg and the usable routes of administration may be chosen from intraspinal, intrathecal, intraventricular, epidural, intraparenchymal, intravitreal, transphenoidal or topical routes.

Other routes of administration known to those skilled in the art may also be used such as subcutaneous, intravenous, intraluminal, or intranasal routes. When one or more of these routes of administration are used, the doses to be used may range from 1 µg/kg to 50 mg/kg.

These medicaments or compositions are intended, in particular, for the treatment of neurodegenerative diseases and/or the regeneration of central nervous system cells (brain, spinal cord) or peripheral nerves after trauma. Their use in the regeneration of the cells of the nervous system may be effected either by direct administration to a patient or extracorporeally. These medicaments or compositions may, in particular, be used in the treatment of Alzheimer's disease, multiple sclerosis, Parkinson's disease, or any other neurodegenerative pathology, or accidental or traumatic type pathologies such as spinal cord lesions, head trauma or strokes. These medicaments or compositions may also be used in the treatment of auditory, optic, olfactory nerves, or any cranial or peripheral nerve lesions whether of traumatic, accidental or degenerative origin.

According to another aspect, the invention relates to a polypeptide such as described above, for its use in the treatment of neurodegenerative pathologies or trauma in which regeneration of the central nervous system is sought. The polypeptide according to the present invention may be used for the treatment of lesions, traumatic or not, of the peripheral nervous system.

According to another advantageous embodiment, the invention relates to a polypeptide as previously described for its use in the treatment of pathologies of the accidental, traumatic or degenerative type, in particular Alzheimer's disease, multiple sclerosis, Parkinson's disease, strokes, spinal cord injury, head trauma or damage to the optic, olfactory, auditory nerves or any cranial or peripheral nerve.

The term SEM means the standard error of the mean.

Figure 6:
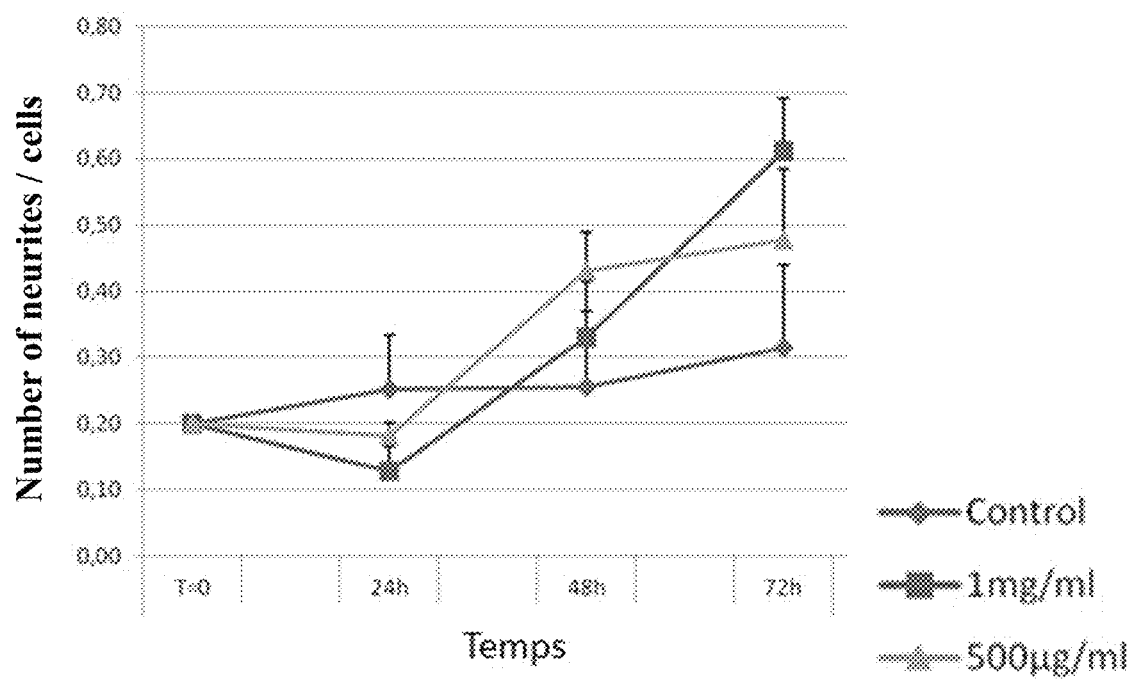

FIG. 6 shows the quantification of the effect of the cyclic polypeptide of sequence SEQ ID NO: 2 on the number of neurites. The average number of sproutings per B104 cell is analyzed after 1, 2 or 3 days of culture. The values are mean±SEM (n=3). The cells are cultured in a serum-free medium (control), or a serum-free medium containing cyclic polypeptide of sequence SEQ ID NO: 2 at concentrations of 1 mg/ml or 500 µg/ml.

Figure 7:
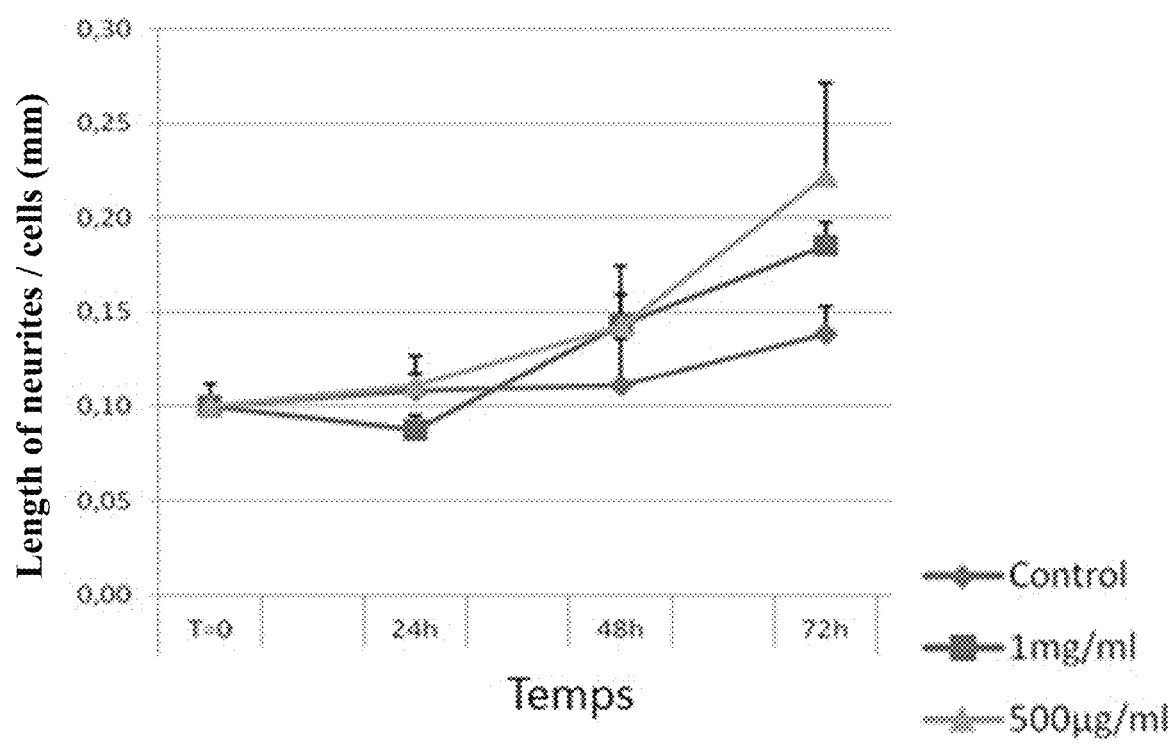

FIG. 7 shows the quantification of the effect of the cyclic polypeptide of sequence SEQ ID NO: 2 on the length of the neurites. The average neurite length per B104 cells is analyzed after 1, 2 or 3 days of culture. The values are mean±SEM (n=3). The cells are cultured in a serum-free medium (control) or a serum-free medium containing cyclic polypeptide of sequence SEQ ID NO: 2 at concentrations of 1 mg/ml or 500 µg/ml.

Figure 8:
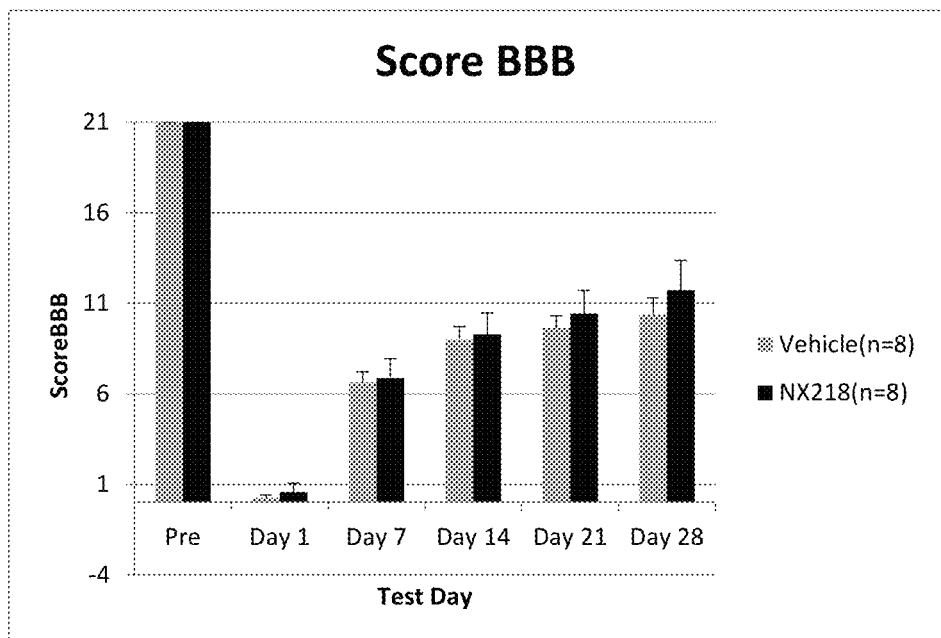

FIG. 8 shows the result of the evaluation of the locomotor performances studied using the Basso, Beattie, Bresnahan (BBB) scale (Basso D M et al. Neurotrauma, 12, 1-21, 1995, Basso D M et al. Exp Neurol, 139, 244-256, 1996). The values are the mean±SEM. The BBB scores range from 0 (no posterior leg movement) to 21 (normal walking with coordination and parallel leg placement).

Figure 9:
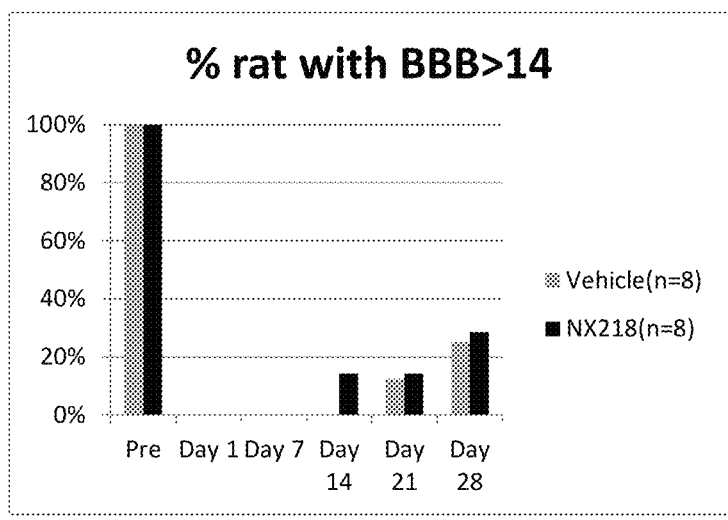

FIG. 9 shows the percentage of rats for which the BBB score is greater than or equal to 14.

Figure 10:
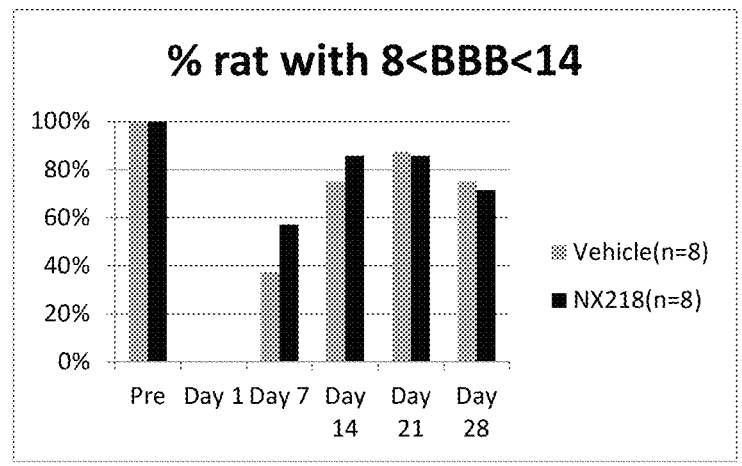

FIG. 10 shows the percentage of rats for which the BBB score is greater than or equal to 8 and less than 14.

Figure 11:
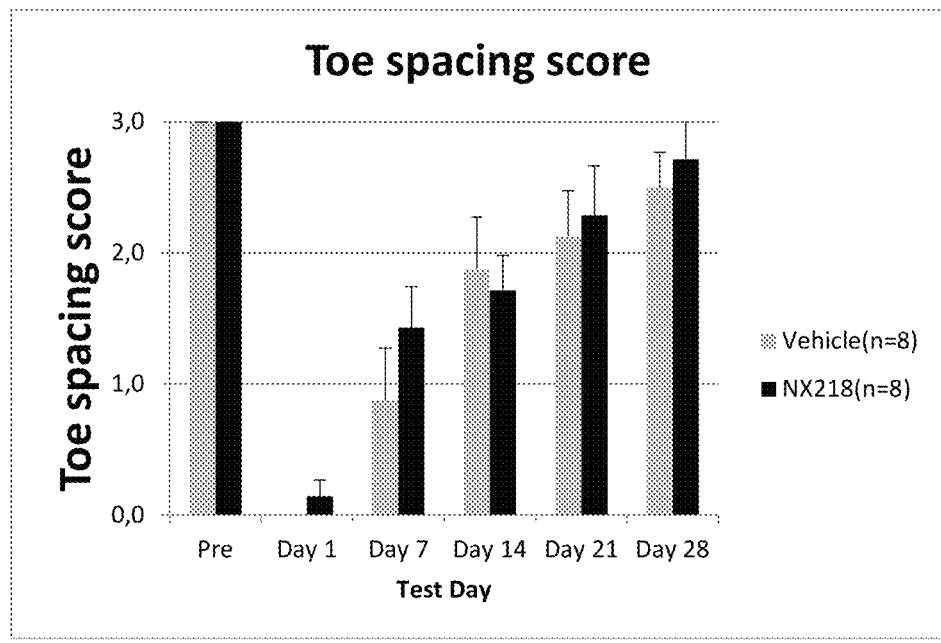

FIG. 11 shows the result of the evaluation of the reflex activities of spacing of the toes. The scores considered are: 0=no reflex activity, 1=considerably weaker than normal, 2=slightly weaker than normal, 3=normal.

Figure 12:
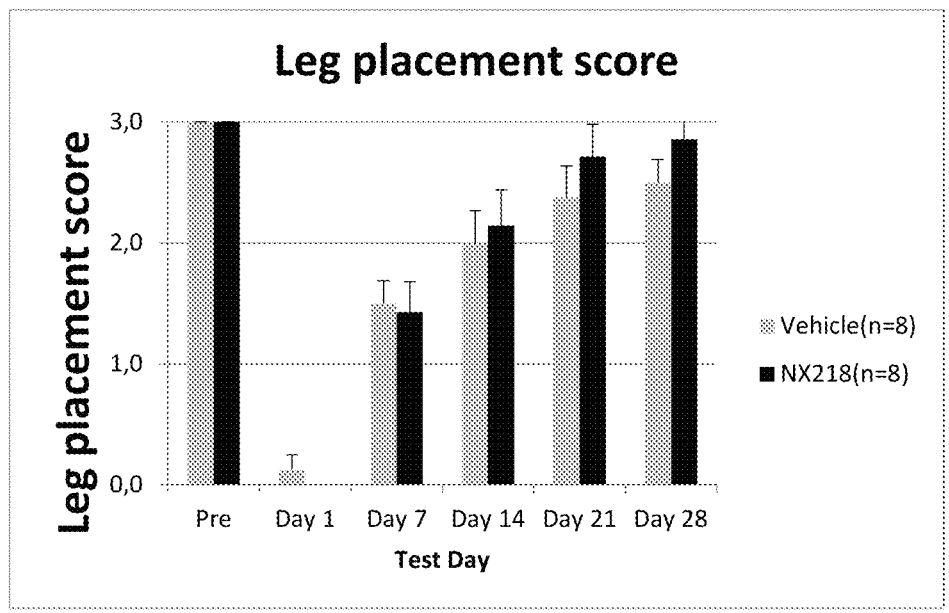

FIG. 12 shows the result of the evaluation of the placing of the hind legs. The scores considered are: 0=no reflex activity, 1=considerably weaker than normal, 2=slightly weaker than normal, 3=normal.

Figure 13:
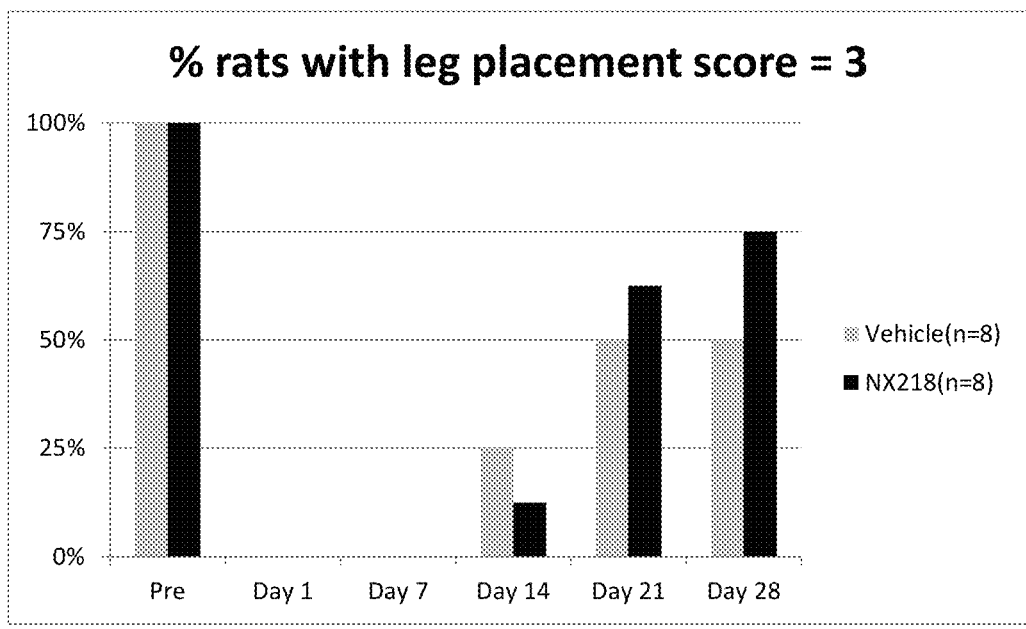

FIG. 13 shows the percentage of the rats for which the score of the placing of the hind legs is equal to 3 (normal).

Figure 14:
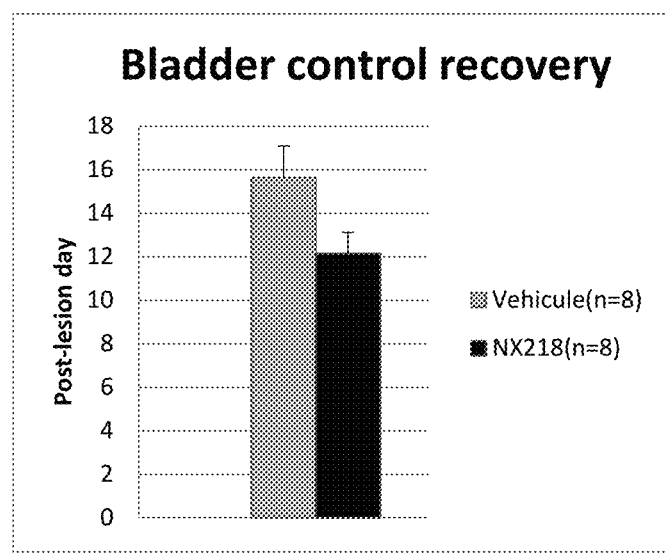

FIG. 14 shows the average of the day on which the rats recovered bladder control. The values are the mean±SEM.

EXAMPLES

Example 1: Synthesis Methods of the Polypeptide of Sequence W-S-G-W-S-S-C-S-R-S-C-G in which the 2 Cysteines are Linked by a Disulfide Bridge (SEQ ID NO: 2)

1) Oxidation of the Polypeptide of Sequence W-S-G-W-S-S-C-S-R-S-C-G (SEQ ID NO: 58) in the Presence of Human Albumin To carry out this synthesis, we put the polypeptide of sequence W-S-G-W-S-S-C-S-R-S-C-G (SEQ ID NO: 58) with different amounts of albumin so that the ratios of polypeptide sequence SEQ ID NO: 58: human albumin (HSA) are in the order of 1:100, 1:10 and 1:1.

Starting from the polypeptide of sequence W-S-G-W-S-S-C-S-R-S-C-G (SEQ ID NO: 58) put in the presence of a 1:1 ratio of HSA and incubated for 1 to 3 hours at room temperature with stirring in air, we observed by HPLC, the formation of a peak corresponding to the polypeptide of sequence W-S-G-W-S-S-C-S-R-S-C-G in which the 2 cysteines are linked by a disulfide bridge (SEQ ID NO: 2). After removal of the albumin by precipitation, the product is then purified and analyzed by HPLC. The use of a different ratio of albumin and of polypeptide corresponding to the sequence SEQ ID NO: 58 makes it possible to influence the cyclization rate and the final yield of cyclisation, while knowing that a smaller amount of albumin is easier to eliminate.

2) Another Method for Preparing the Polypeptide Corresponding to the Sequence SEQ ID NO: 2 while Avoiding the Separation and Prior Purification of the Linear Polypeptide (Polypeptide of Sequence SEQ ID NO: 58)

The polypeptide of sequence W-S-G-W-S-S-C-S-R-S-C-G (SEQ ID NO: 58) is synthesized on a resin in a manner similar to the conventional method set forth in International Patent Application WO 1999/03890 but without cleaving or detaching it from the resin. This makes it possible to avoid two steps that are expensive in time and money, and which consists in isolating, then purifying the polypeptide before returning it to solution in order to oxidize it to the desired product corresponding to the sequence SEQ ID NO: 2. The oxidation in the presence of albumin is effected directly with the polypeptide of sequence W-S-G-W-S-S-C-S-R-S-C-G (SEQ ID NO: 58) linked to the resin. The purification is similar to that described in the example above but the albumin separation step is easier because it is carried out by simple washing, while the polypeptide is still attached to the resin. Once the albumin has been removed, then the polypeptide may be detached from the resin by conventional methods.

Example 2: Effect of Albumin on the Cyclization of the Polypeptide of Sequence W-S-G-W-S-S-C-S-R-S-C-G (SEQ ID NO: 58), i.e. its Transformation into a Polypeptide of Sequence W-S-G-W-S-S-C-S-R-S-C-G in which the 2 Cysteines are Linked by a Disulfide Bridge (SEQ ID NO: 2)

We investigated the behavior of the polypeptide of sequence W-S-G-W-S-S-C-S-R-S-C-G (SEQ ID NO: 58) in the absence and presence of human albumin (HSA) and the resulting formation of the polypeptide sequence W-S-G-W-

S-S-C-S-R-S-C-G in which the 2 cysteines are linked by a disulfide bridge (SEQ ID NO: 2).

The method is as follows:

A solution containing the polypeptide of sequence W-S-G-W-S-S-C-S-R-S-C-G (SEQ ID NO: 58) at 50 µg/ml was prepared in PBS and 5% glucose in the presence or absence of HSA at 2.5 mg/ml.

The ratio of polypeptide of sequence W-S-G-W-S-S-C-S-R-S-C-G (SEQ ID NO: 58): HSA is of the order of 1:1, and therefore equimolar.

The solutions were mixed and injected directly by reverse phase HPLC using a method using the Phenomenex Jupiter 300 Å column and elution solvents consisting of HPLC water with 0.1% trifluoroacetic acid and acetonitrile with 0.1% trifluoroacetic acid to allow separation of the HSA peaks, the polypeptide of sequence W-S-G-W-S-S-C-S-R-S-C-G (SEQ ID NO: 58) and the polypeptide of sequence W-S-G-W-S-S-C-S-R-S-C-G in which both cysteines form a disulfide bridge (SEQ ID NO: 2).

This operation was repeated at T=0 min and at T=60 min.

The chromatographic profiles allowed the following observations:

In 60 minutes, in the absence of albumin (HSA) and thus by air oxidation, the peak of the polypeptide of sequence W-S-G-W-S-S-C-S-R-S-C-G in which the two cysteines form a disulfide bridge (SEQ ID NO: 2), increased by 9.1% relative to the original peak of the polypeptide sequence SEQ ID NO: 58.

Under identical conditions, but in the presence of albumin, at T=60 min, the peak of the polypeptide of sequence W-S-G-W-S-S-C-S-R-S-C-G in which the two cysteines form a disulfide bridge (SEQ ID NO: 2) increased by 38% relative to the starting peak of the polypeptide sequence SEQ ID NO: 58.

This result shows an accelerating effect of albumin in the cyclization of the polypeptide of sequence SEQ ID NO: 58 which leads to the formation of the polypeptide sequence W-S-G-W-S-S-C-S-R-S-C-G in which both cysteines form a disulfide bridge (SEQ ID NO: 2).

In the absence of albumin, in 60 minutes, 25% of the peak of the polypeptide of sequence SEQ ID NO: 58 is transformed into a polypeptide of sequence W-S-G-W-S-S-C-S-R-S-C-G in which the two cysteines form a sulfide bridge (SEQ ID NO: 2)

In the presence of albumin and under the same conditions, in 60 minutes, 54% of the polypeptide of sequence SEQ ID NO: 58 is transformed into a polypeptide of sequence W-S-G-W-S-S-C-S-R-S-C-G in which the two cysteines form a disulfide bridge (SEQ ID NO: 2)

This result shows that in the presence of albumin, a greater amount of the product corresponding to SEQ ID NO: 2 is formed in comparison with the air oxidation, which corresponds to higher specificity and purity in favor of albumin.

Discussion

The two experiments described in this example demonstrate the important role of albumin in producing the polypeptide of sequence W-S-G-W-S-S-C-S-R-S-C-G in which both cysteines form a disulfide bridge (SEQ ID NO: 2) from the polypeptide of sequence W-S-G-W-S-S-C-S-R-S-C-G. (SEQ ID NO: 58) compared with air oxidation. The reaction is, in fact, at least 2 times faster, preferably 5 times faster, and more preferably 10 times faster depending on the peptide/albumin ratios in air. In the example indicated above, the formation of 9.1% without albumin versus 38% with albumin is observed, therefore the reaction is here about 4 times faster and it is also carried out with a better specificity (25% without albumin compared to 54% with albumin), which corresponds to greater purity. In fact, in 60 minutes, 25% of transformation of the polypeptide of sequence W-S-G-W-S-S-C-S-R-S-C-G (SEQ ID NO: 58) in the absence of albumin corresponds to the possible formation of 75% impurities and, in the presence of albumin, 54% of transformation of the polypeptide of sequence W-S-G-W-S-S-C-S-R-S-C-G (SEQ ID NO: 58) corresponds to the formation of only 46% of impurities.

Example 3: Effect of the Ratios of the Polypeptide of Sequence W-S-G-W-S-S-C-S-R-S-C-G (SEQ ID NO: 58) Relative to Albumin on the Efficiency of Cyclization of the Polypeptide of Sequence W-S-G-W-S-S-C-S-R-S-C-G (SEQ ID NO: 58) to the Polypeptide of Sequence W-S-G-W-S-S-C-S-R-S-C-G in which the 2 Cysteines are Linked by a Disulfide Bridge (SEQ ID NO: 2)

Example 2 showed how an equimolar ratio (identical molar ratio) of albumin and polypeptide made it possible to obtain a greater amount of polypeptide corresponding to the of sequence SEQ ID NO: 2 from the polypeptide of sequence SEQ ID NO: 58 and with superior purity. The example below describes how different ratios of albumin and polypeptide influence the rate of disulfide bond formation, and the purity of the polypeptide of sequence SEQ ID NO: 2.

Three quantities of polypeptide of sequence W-S-G-W-S-S-C-S-R-S-C-G (SEQ ID NO: 58) are incubated for approximately 1 hour at 37° C. in the same volume of rat cerebrospinal fluid in which there is a constant physiological amount of albumin and the rate of formation of the cyclic polypeptide of sequence W-S-G-W-S-S-C-S-R-S-C-G in which the two cysteines form a disulfide bridge (SEQ ID NO: 2), is observed by HPLC. The study seeks to demonstrate the influence of the polypeptide: albumin ratio on the cyclization rate of the linear polypeptide of sequence SEQ ID NO: 58 measured by Tmax.

Tmax, corresponding to the time when the greatest amount of cyclic polypeptide of sequence W-S-G-W-S-S-C-S-R-S-C-G in which both cysteines form a disulfide (SEQ ID NO: 2), is formed, is given in Table 1.

The ratios corresponding to the various doses of polypeptide of sequence SEQ ID NO: 58 added are indicated in Table 1.

TABLE 1

Effect of the ratios of polypeptide of sequence SEQ ID NO: 58: albumin on the Tmax of the cyclization reaction of the polypeptide of sequence SEQ ID NO: 58 in polypeptide of sequence SEQ ID NO: 2

| | Cyclization in the presence of albumin | | |
|---|---|---|---|
| Mass of polypeptide of sequence SEQ ID NO: 58 added (mg) | 6.00 | 60 | 600 |
| Ratio polypeptide:albumin | 2:1 | 20:1 | 200:1 |
| Tmax (min) | 10 | 30 | 120 |

Conclusion: A catalyst effect for albumin is observed, as exemplified by the ratios presented in Table 1 which demonstrate the involvement of albumin in the acceleration of cyclization. In fact, a very slight difference in the amount of albumin placed in the presence of the polypeptide (as represented by the ratios 20:1 and 200:1) makes it possible to accelerate the cyclization and consequently reduce its Tmax from 120 to 30 minutes.

To conclude, there is a correlation between the ratio of the polypeptide of sequence W-S-G-W-S-S-C-S-R-S-C-G (SEQ ID NO: 58) relative to albumin and the kinetics of cyclization. In fact, the smaller the ratio of polypeptide:albumin, so the faster is the reaction. In other words, the closer the ratio of polypeptide to albumin is to 1:1, the faster is the reaction. Finally, a small amount of albumin is sufficient to accelerate the cyclization reaction and disulfide formation (catalyst effect).

Alternatively, the cyclization and production of disulfide in the presence of albumin may be effected in the complete absence of air or in the presence of a very small amount of air, and therefore of oxygen, which may make it possible to avoid the formation of contaminant products from uncontrolled oxidation reactions.

Example 4: Study of the Solubility of the Cyclic Polypeptide of Sequence W-S-G-W-S-S-C-S-R-S-C-G in which the Two Cysteines Form a Disulfide Bridge (SEQ ID NO: 2) in Aqueous NaCl Solution Two weighings of 0.5 mg are made in a 1.5 ml micro tube for the polypeptide

(SEQ ID NO: 58)

and the polypeptide:

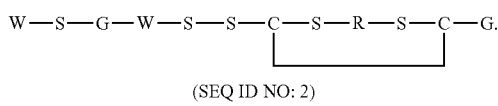
(SEQ ID NO: 2)

Figure 1:
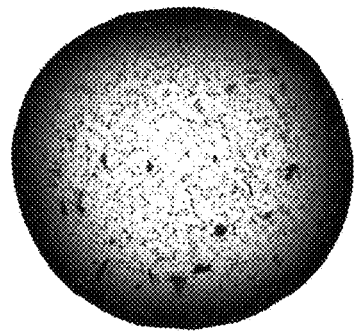
FIG. 1 shows the optical microscope observation of a drop of a solution of the polypeptide of sequence SEQ ID NO: 58 (A, magnification ×25, B, magnification ×100) and the polypeptide sequence SEQ ID NO: 2 (C, magnification ×25) at a concentration of 29.4 mg/ml in 0.9% NaCl.
Figure 1:
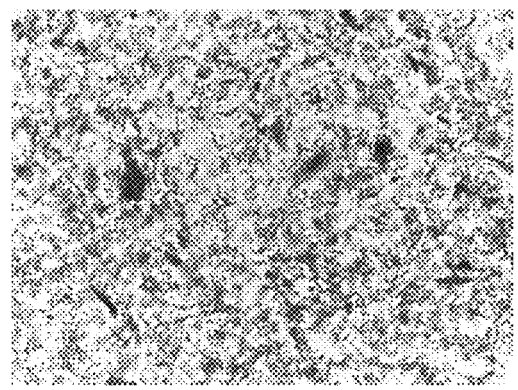
Figure 1:
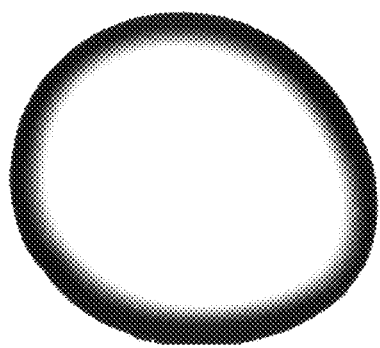

17 microliters of a 0.9% NaCl solution previously prepared are added in each tube, in order to produce a peptide solution at 29.4 mg/ml. The tubes are then vortexed for a few seconds and one drop of each polypeptide solution so obtained is placed on a glass slide for observation under an optical microscope. Under these conditions, only the polypeptide of sequence SEQ ID NO: 2 appears to be soluble without any visible particle or cluster (FIG. 1). The polypeptide of sequence SEQ ID NO; 58 has a large number of particles.

The solubility limit of the polypeptide of sequence SEQ ID NO: 58 in an aqueous 0.9% NaCl solution is determined at about 2 mg/ml under a microscope and by visual examination.

The solubility of the polypeptide of sequence SEQ ID NO: 2 in 0.9% NaCl is estimated to be greater than 29 mg/ml by visual examination.

The solubility limit of the polypeptide of sequence SEQ ID NO: 2 in a 0.9% NaCl solution is therefore at least 15 times greater than that of the polypeptide sequence SEQ ID NO: 58 in the same solution.

Example 5: Greater Stability of the Polypeptide W-S-G-W-S-S-C-S-R-S-C-G Wherein the 2 Cysteines are Linked by a Disulfide Bond (SEQ ID NO: 2) Compared with W-S-G-W-S-S-C-S-R-S-C(SEQ ID NO: 58) in the Presence of Enzymes Enzymatic digestion was performed using neprylysine incubated with the purified form of the polypeptide of interest either in its linear form (SEQ ID NO: 58) or in its cyclic form (SEQ ID NO: 2). The time parameters (t=0 and t=30 minutes) were explored with an enzyme diluted by a tenth in water. A so-called "control" sample without enzyme and effected in parallel was performed to establish an analytical reference for each parameter explored.

The polypeptides are diluted in deoxygenated water to maintain the stability of both forms over time. Digestions were analyzed by the LC/MS/MS mass spectrometry technique.

The results (areas under the curve and percentage of digestion) are presented in Table 2. The percentage of digestion corresponds, for a given polypeptide, to the percentage of the area under the curve in the presence of enzyme relative to the area under the control curve for the same polypeptide.

TABLE 2

Areas under the curve measured after analysis of the polypeptide digestion with neprylysine by LC/MS/MS and digestion percentage for the polypeptide of sequence SEQ ID NO: 58 and the polypeptide of sequence SEQ ID NO: 2.

| | | Polypeptide of sequence SEQ ID NO: 58 | Polypeptide of sequence SEQ ID NO: 2 |
|---|---|---|---|
| T = 0 min | Area under the control curve (no enzyme) | 788400 | 3008000 |
| | Area under the curve in the presence of enzyme | 797200 | 3220000 |
| | Percentage of digestion | none | none |
| T = 30 min | Area under the control curve (no enzyme) | 802800 | 3722000 |
| | Area under the curve in the presence of enzyme | 576500 | 3401000 |
| | Percentage of digestion | 28% | 8.5% |

Conclusion: At t=0, the two polypeptides appear stable in the presence of neprilysine. At t=30 min, the cyclic peptide (SEQ ID NO: 2) is more stable than the linear polypeptide (SEQ ID NO: 58) (28% digestion versus 8.5%).

Example 6: Separation of the Two Peaks Corresponding to the Polypeptides of SEQ ID NO: 2 and SEQ ID NO: 58 Showing the Conformational Difference A synthesis of polypeptide sequence SEQ ID NO: 2 from polypeptide SEQ ID NO: 58 in the presence of human albumin is carried out. Two HPLC analyzes of the compounds present are made during the synthesis reaction: the first at T=0 minutes, and the second at T=60 minutes. The chromatograms obtained are presented superimposed in FIG. 2.

The analytical conditions used for the separation of the compounds are as follows:
Column: XBridge® C18, 2.1×100 mm, 3.5 μm
Mobile phase: A: acetonitrile with 0.1% TFA (trifluoroacetic acid)
B: distilled water containing 0.1% TF A
Elution rate: 0.500 mL/min
Gradient:

| Time (min) | A % | B % |
|---|---|---|
| 0 | 10 | 90 |
| 11 | 25 | 75 |
| 21 | 10 | 90 |

Figure 2:
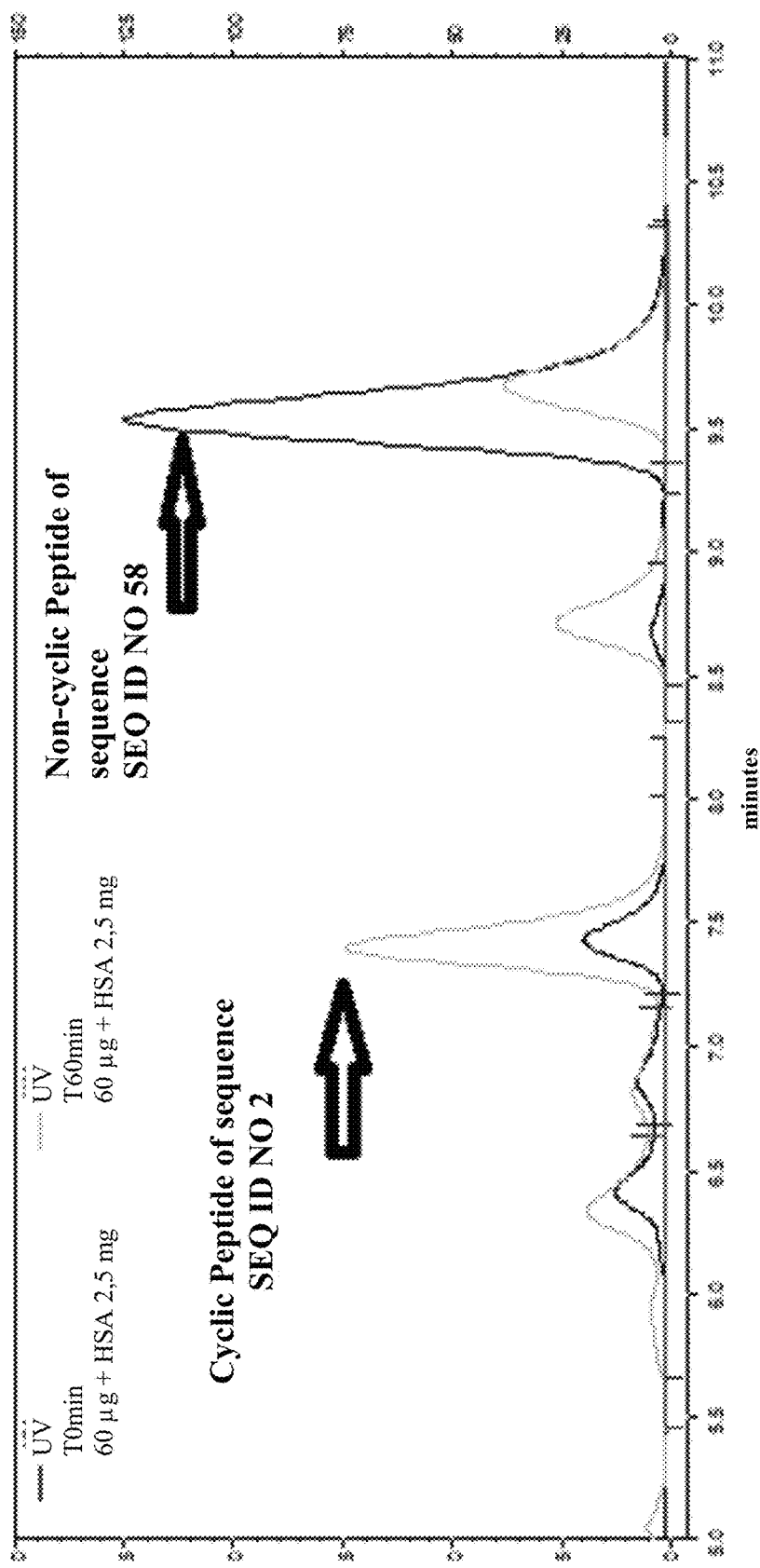
FIG. 2 shows the superimposed chromatograms of the cyclization reaction of the polypeptide of sequence SEQ ID NO: 58 in polypeptide of sequence SEQ ID NO: 2 in the presence of human albumin made at the initiation of the reaction (T0 min) and after 60 minutes of cyclization reaction (T60 min).
Figure 3:
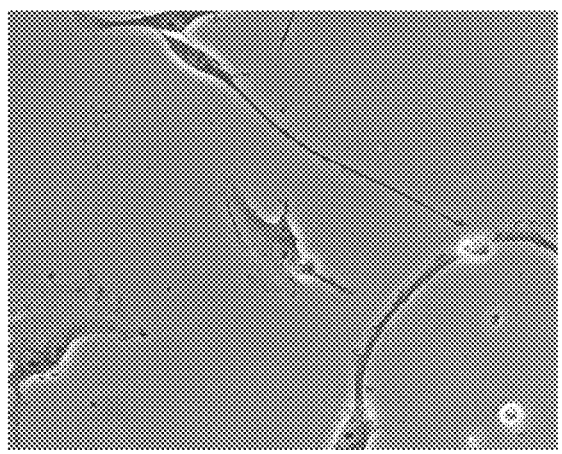
FIG. 3 shows the optical phase contrast microscope observation (magnification ×400) of the effect of the cyclic polypeptide of sequence SEQ ID NO: 2 on B104 cells after 48 h. The cells are cultured for 2 days in a serum-free medium and in the absence (A) or presence (B) of the cyclic polypeptide of sequence SEQ ID NO: 2 at 1 mg/ml.
Figure 3:
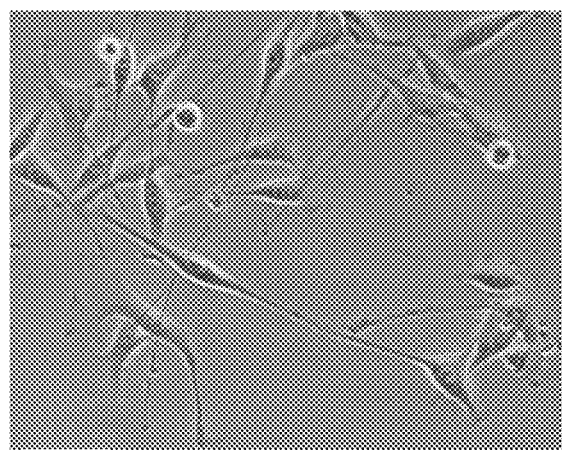
Figure 4:
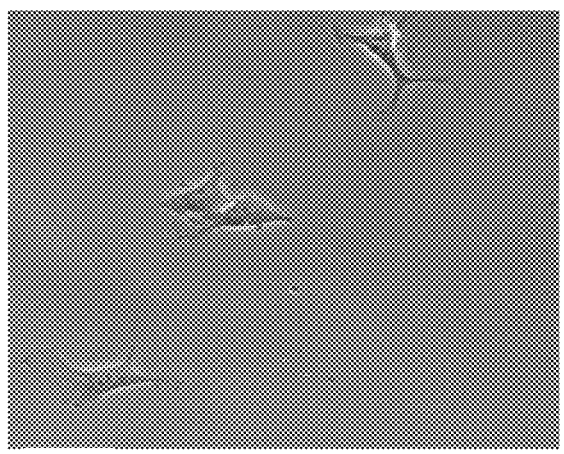
FIG. 4 shows the phase-contrast optical microscope observation (magnification ×400) of the effect of the cyclic polypeptide of sequence SEQ ID NO: 2 on the B104 cells after 72 h. The cells are cultured for 3 days in a serum-free medium and in the absence of (A) or in the presence (B) of cyclic polypeptide of sequence SEQ ID NO: 2 at 500 µg/ml.
Figure 4:
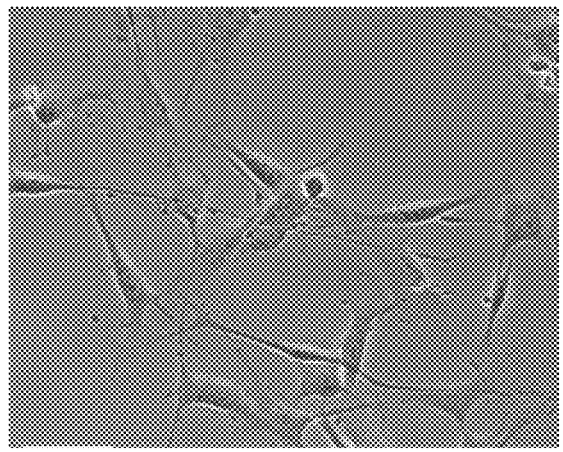
Figure 5:
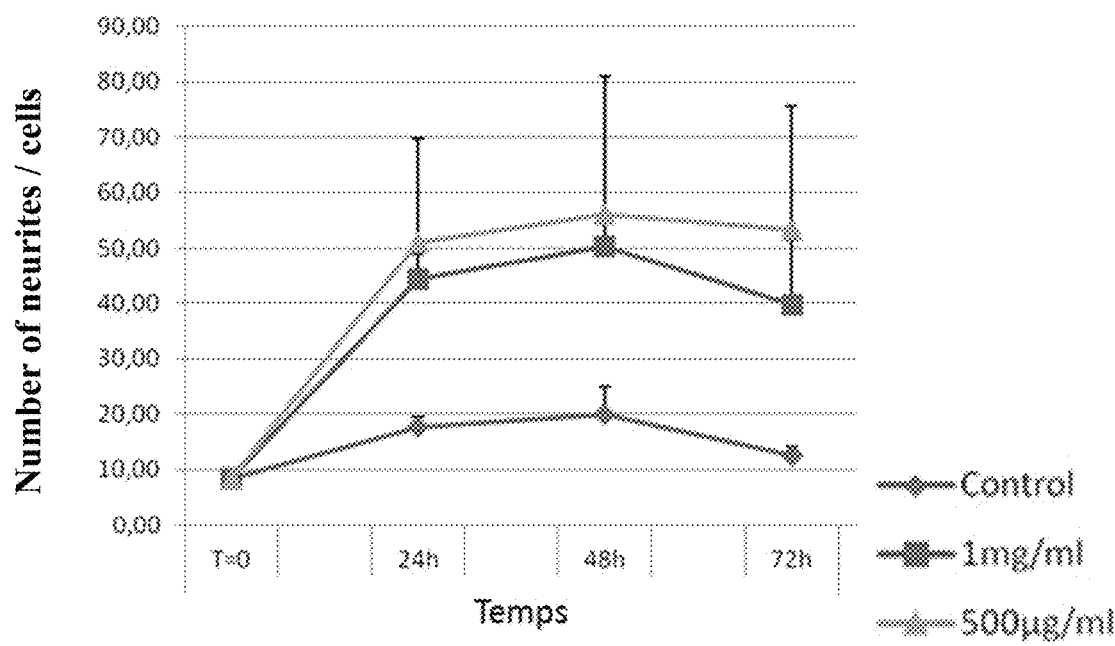
FIG. 5 shows the quantification of the effect of the cyclic polypeptide of sequence SEQ ID NO: 2 on the number of cells. The average number of B104 cells is analyzed after 1, 2 or 3 days of culture. The values are average±SEM (n=3). The cells are cultured in a serum-free medium (control) or a serum-free medium containing the cyclic polypeptide of sequence SEQ ID NO: 2 at concentrations of 1 mg/ml or 500 µg/ml.

FIG. 2 shows that the peaks corresponding to the polypeptides SEQ ID NO: 2 (cyclic) and SEQ ID NO: 58 (linear, non-cyclic) may be easily separated.

Example 7: In Vitro Pharmacology

Neuroblastoma cells of the B104 line are cultured in a flask of 75 cm$^2$ at 37° C. under 5% of $CO_2$ in Dulbecco's Modified Eagle's Medium (DMEM) supplemented with 2 mM glutamine, penicillin G at 50 U/ml, streptomycin sulfate 50 µg/ml and 10% fetal bovine serum (FBS). The cells are seeded in 48-well plates coated with a poly-D-lysine matrix at 10 µg/ml to obtain a final cell density of 5000 cells/well. Four hours after inoculation, the culture medium is replaced with medium without FBS at the rate of 200 µl/well containing, or not, cyclic polypeptide of sequence SEQ ID NO: 2 at a concentration of 1000, 500, 375 or 150 µg/ml. The culture medium is no longer changed during the entire duration of the experiment. The absence of serum will then induce an initiation of the differentiation of B104 with appearances of more or less important neuritic extensions.

To quantify the effects of the cyclic polypeptide of sequence SEQ ID NO: 2 on the cultures, the cells are observed after 1, 2 and 3 days of culture in randomly selected fields under a phase contrast microscope using a grid lens (1×1 cm, divided into 1×10 cm squares and ×400 magnification. Each well is counted in triplicate for each experiment and 3 fields per well are examined. The parameters analyzed are the number of cells, the number of neurites (cell extension at least as large as the cell diameter of the cell) per cell and the average length of the 10 longest neurites.

Under these conditions, it is observed that: The cyclic peptide of sequence SEQ ID NO: 2 has an effect on the number of B104 cells:

Under standard conditions, i.e. in the absence of the polypeptide of sequence SEQ ID NO: 2, the growth of B104 cells increases for 48 hours before the number of cells starts to decrease due to the absence of serum and a depletion of the culture medium. However, in the presence of the cyclic polypeptide of sequence SEQ ID NO: 2, the number of cells is increased as of 24 h with 5 times more cells compared to the control condition.

Examples of growth of B104 cells are shown in FIGS. 2, 3, 4 and 5.

The cyclic polypeptide of sequence SEQ ID NO: 2 has an effect on the morphology of B104 cells:

While B104 cells have fibroblastic morphology when cultured in the presence of serum, they engage in neuronal differentiation when cultured in the absence of serum. At 24 h, in serum-free culture and regardless of the presence or absence of differentiating factors, the B104 cells show mono or bipolar expansions as well as sprouting (small extensions less than the diameter of the cell body) and neurites (cellular extensions at least as large as the diameter of the cell body), i.e. a morphology typical of these conditions (Schubert D et al., Nature 249 (454), 224-227 1974).

The cyclic polypeptide of sequence SEQ ID NO: 2, whatever its concentration, has no effect on the number of sproutings. However, the presence of the cyclic polypeptide of sequence SEQ ID NO: 2 increases the number of leurites per cell (FIG. 6) and their lengths (FIG. 7).

After 3 days of culture, the treated B104s have developed significant neuritic extensions which have grown as the culture time increases. This effect on neurite length appears dose-dependent.

Example 8: In Vivo Pharmacology—Evaluation on a Model of Medullary Lesion

The contusion model is recognized and used to mimic the spinal cord injury observed in humans (Young W., Prog Brain Res., 137, 231-55, 2002).

This model is used to evaluate the effectiveness of active principles on functional recovery. Experiments were performed on adult female Sprague-Dawley rats of approximately 250 g. The surgical procedure is carried out under general anesthesia with 5% isoflurane (in 70% $N_2O$ and 30% $O_2$, flow rate 300 ml/min).

After laminectomy at the thoracic vertebrae T9 and T10, the spinal cord injury is obtained using an electromagnetic device (PinPoint system, Hatteras Inc., USA) to obtain a calibrated contusion (depth 2 mm, diameter of the impactor, 2 mm, moved at the speed 1.5 m/s for 85 ms) (according to Bilgen M. Neurorehab et al., 19(3), 2005).

Within 15 minutes following the trauma, 3 µl of the cyclic polypeptide of sequence SEQ ID NO: 2 at a concentration of 7 µg/ml or the vehicle is injected by means of a Hamilton syringe (10 pi, model 1701) and a micro-infusion system (Harvard Apparatus) allowing injection into the intra-spinal space. After injection, the needle is left in place for 5 minutes. As soon as the needle is withdrawn, a cellular adhesive is applied to the injection site to seal the dura and avoid any leakage of biological fluid. After suturing, the rats are housed individually in standard cages at a temperature of 22° C.±1° C. under controlled lighting (12 h/day), water and food ad libitum. A second injection is carried out 2 days later. Behavioral tests are performed on each animal observed individually, in blind manner.

The locomotor performances are studied using the Basso, Beattie, Bresnahan (BBB) scale (Bassa D M et al., J. Neurotrauma, 12, 1-21, 1995, Basso D M et al., Exp Neurol, 139, 244-256, 1996).

Each animal is evaluated before the trauma and then once a week. At the same time, each animal is weighed before the trauma and then once a week.

In the evaluation scale of locomotion: the BBB scores, i.e. the statistical data, are expressed by their mean±SEM.

The BBB scores range from 0 (no posterior leg movement) to 21 (normal walking with coordination and parallel leg placing). Scores from 0 to 7 indicate the return of isolated movements of the three posterior leg (ankle, knee, hip), 8 to 13 indicate the return of posterior leg placement and coordination with the forelegs, 14 to 21 indicate the return of the toe spacing, the position of the legs and the tail, and the stability of the trunk.

Evaluation of the BBB scores is performed before injury, and then at days 1, 7, 14, 21, and 28 post-treatment by two independent observers (FIG. 8, 9, 10).

The reflex activities of toe spacing (FIG. 11) and posterior leg placement (FIGS. 12 and 13) are analyzed on days 1, 7, 14, 21 and 28 post-treatment. The scores considered are: 0=no reflex activity, 1=considerably weaker than normal, 2=slightly weaker than normal, 3=normal.

The day of return of bladder control is also a measured parameter (FIG. 14).

The invention claimed is:

1. Polypeptide comprising the amino acid sequence SEQ ID NO: 59,
   wherein the two cysteines form a disulfide bridge; and
   wherein the polypeptide is substantially free of the reduced or dimeric or oligomeric forms of the polypeptide as well as derivatives of the polypeptide in which the thiol groups are in the sulfoxide or sulfone form.

2. Polypeptide according to claim 1 wherein the amino acid sequence comprises SEQ ID NO: 1.

3. Polypeptide according to claim 1 wherein the amino acid sequence comprises SEQ ID NO: 2.

4. A pharmaceutical composition of comprising as active ingredient a polypeptide according to claim 3 and one or more pharmaceutically-acceptable excipients.

5. The pharmaceutical composition of claim 4 further comprising a second polypeptide comprising the amino acid sequence SEQ ID NO: 59
   wherein the two cysteines form a disulfide bridge; and
   wherein the second polypeptide is substantially free of the reduced or dimeric or oligomeric forms of the second polypeptide as well as derivatives of the second polypeptide in which the thiol groups are in the sulfoxide or sulfone form.

6. Polypeptide according to claim 1 wherein the polypeptide consists of the amino acid sequence SEQ ID NO: 69.

7. Polypeptide according to claim 1 wherein the polypeptide consists of the amino acid sequence SEQ ID NO: 2.

8. Polypeptide according to claim 7,
   wherein the polypeptide has a purity greater than 80%.

9. Polypeptide according to claim 1 wherein the polypeptide consists of the amino acid sequence SEQ ID NO: 59 and
   wherein the polypeptide has a purity greater than 80%.

10. Pharmaceutical composition comprising as active ingredient a polypeptide according to claim 1 and one or more pharmaceutically-acceptable excipients.

11. Method for obtaining the polypeptide of amino acid sequence SEQ ID NO: 59
    having the two cysteines form a disulfide bridge, from a starting polypeptide of sequence SEQ ID NO: 70,
    wherein the starting polypeptide of sequence SEQ ID NO: 70 is in solution;
    comprising forming a disulfide bridge in the presence of albumin in the starting polypeptide of sequence SEQ ID NO: 70.

12. Method according to claim 11 wherein albumin and the starting polypeptide are present in a molar:molar ratio of 1:1 to 1:100.

13. The method of claim 12, wherein said molar:molar ratio is 1:1 to 1:10.

14. The method of claim 12, wherein said molar:molar ratio is 1:1.

15. Method according to claim 11 wherein the forming a disulfide bridge in the presence of albumin in the starting polypeptide is carried out in ambient air.

16. The method according to claim 11, wherein the forming a disulfide bridge in the presence of albumin in the starting polypeptide is carried out without detaching the starting polypeptide from the resin used for the peptide synthesis of these polypeptides, and wherein the polypeptide of sequence SEQ ID NO: 59 is then obtained by separating the polypeptide from the resin after the disulfide bond formation.

17. Method for obtaining the polypeptide of amino acid sequence SEQ ID NO: 2
   from a starting polypeptide of sequence SEQ ID NO: 58:
      comprising forming a disulfide bridge in the presence of albumin in the starting polypeptide of sequence SEQ ID NO: 58.

18. Method according to claim 17, wherein albumin and the starting polypeptide are present in a molar:molar ratio of 1:1 to 1:100.

19. The method of claim 18, wherein said molar:molar ratio is 1:1 to 1:10.

20. The method of claim 18, wherein said molar:molar ratio is 1:1.

21. The method according to claim 17, wherein the forming a disulfide bridge in the presence of albumin in the starting polypeptide is carried out in ambient air.

22. The method according to claim 17, wherein the forming a disulfide bridge in the presence of albumin in the starting polypeptide is carried out without detaching the starting polypeptide from the resin used for the peptide synthesis of the polypeptide, and wherein the polypeptide of sequence SEQ ID NO: 2 is then obtained by separating the polypeptide from the resin after the disulfide bond formation.

* * * * *